US012622573B2

(12) United States Patent (10) Patent No.: US 12,622,573 B2
Kasai et al. (45) Date of Patent: May 12, 2026

(54) ENDOSCOPE AND METHOD OF DISASSEMBLING ENDOSCOPE

(71) Applicant: OLYMPUS MEDICAL SYSTEMS CORP., Tokyo (JP)

(72) Inventors: Yasuaki Kasai, Saitama (JP); Takuya Toyooka, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 308 days.

(21) Appl. No.: 18/384,040

(22) Filed: Oct. 26, 2023

(65) Prior Publication Data

US 2024/0138655 A1 May 2, 2024

Related U.S. Application Data

(60) Provisional application No. 63/420,119, filed on Oct. 28, 2022.

(51) Int. Cl.
| | |
|---|---|
| *A61B 1/00* | (2006.01) |
| *A61B 1/005* | (2006.01) |
| *A61B 1/018* | (2006.01) |

(52) U.S. Cl.
CPC ...... *A61B 1/00128* (2013.01); *A61B 1/00126* (2013.01); *A61B 1/00165* (2013.01); *A61B 1/0057* (2013.01); *A61B 1/018* (2013.01)

(58) Field of Classification Search
CPC ............ A61B 1/00128; A61B 1/00126; A61B 1/00165; A61B 1/0057; A61B 1/018; A61B 1/00105; A61B 1/0011
See application file for complete search history.

(56) References Cited

U.S. PATENT DOCUMENTS

| | | | |
|---|---|---|---|
| 10,088,638 B2 | 10/2018 | Yajima | |
| 2004/0133075 A1* | 7/2004 | Motoki | .............. A61B 1/00147 |
| | | | 600/153 |

FOREIGN PATENT DOCUMENTS

| | | |
|---|---|---|
| JP | 2000-014628 A | 1/2000 |
| JP | 2000-051145 A | 2/2000 |
| JP | 2009-142562 A | 7/2009 |
| JP | 5468845 B2 | 4/2014 |
| JP | 6392372 B2 | 9/2018 |

* cited by examiner

*Primary Examiner* — Timothy J Neal

(74) *Attorney, Agent, or Firm* — Morgan, Lewis & Bockius LLP

(57) ABSTRACT

An endoscope includes an insertion portion, an operation portion, and a fitting mechanism coupling the insertion portion and the operation portion so as to be decouplable. The fitting mechanism includes a plate portion and a convex portion, and a fitted-shape portion and a hole. The convex portion is fitted to the fitted-shape portion. The hole exposes at least one of the plate portion or the convex portion to outside. The fitting mechanism is provided at a position around a center axis, corresponding to a bending wire.

20 Claims, 18 Drawing Sheets

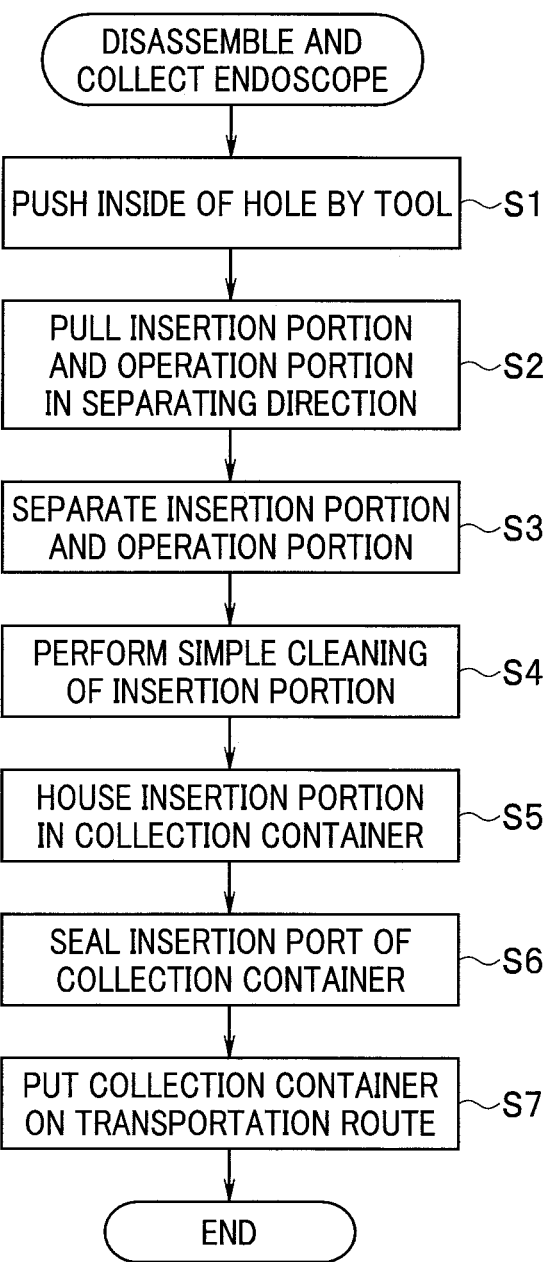

DISASSEMBLE AND
COLLECT ENDOSCOPE

PUSH INSIDE OF HOLE BY TOOL — S1

PULL INSERTION PORTION
AND OPERATION PORTION
IN SEPARATING DIRECTION — S2

SEPARATE INSERTION PORTION
AND OPERATION PORTION — S3

PERFORM SIMPLE CLEANING
OF INSERTION PORTION — S4

HOUSE INSERTION PORTION
IN COLLECTION CONTAINER — S5

SEAL INSERTION PORT OF
COLLECTION CONTAINER — S6

PUT COLLECTION CONTAINER
ON TRANSPORTATION ROUTE — S7

END

ENDOSCOPE AND METHOD OF DISASSEMBLING ENDOSCOPE

RELATED APPLICATION DATA

This application is based on and claims priority under 35 U.S.C. § 119 to U.S. Provisional Application No. 63/420,119 filed on Oct. 28, 2022, the entire contents of which are incorporated herein by reference.

FIELD OF THE DISCLOSURE

The disclosure relates to an endoscope in which an insertion portion and an operation portion can be coupled and decoupled, and to a method of disassembling the endoscope.

BACKGROUND

A single-use endoscope that is collected by a manufacturer, a collection trader, or the like and is disassembled and discarded after being used only once has been proposed.

In a case where a whole of the endoscope is used only once, a cost for single use is increased. Therefore, a separable endoscope in which an insertion portion and an operation portion can be coupled and decoupled has been proposed. In the case of the separable endoscope, the insertion portion is used only once, and the operation portion is reused.

For example, in a separable endoscope disclosed in Japanese Patent Application Laid-Open Publication No. 2009-142562, a coupling/decoupling mechanism holding fitting of T-shaped concave/convex portions with friction force enables attachment/detachment of an operation portion and an insertion portion. The T-shaped concave/convex portions are fitted by being moved in a direction perpendicular to a center axis of the insertion portion. Wire pieces are coupled to rear end parts of angle wires provided inside the insertion portion. When the wire pieces are fitted to grooves provided in rack members of the operation portion, the angle wires and the wire pieces are coupled. An observation unit that illuminates and picks up an image of an observation subject is incorporated in a distal end hard portion of the insertion portion.

When the single-use insertion portion includes an image pickup device and the like in the separable endoscope, the image pickup device that is relatively high in cost is used only once.

A hybrid endoscope in which an optical image is transmitted from a distal end portion of an insertion portion through an image guide, and the optical image is picked up by an image pickup device provided inside an operation portion is known. The hybrid endoscope has advantages of both of high insertion property of a fiber scope and high image quality of a video scope. When a whole of the hybrid endoscope is used only once, the image pickup device that is relatively high in cost is also used only once.

SUMMARY OF THE DISCLOSURE

An endoscope according to an aspect of the present disclosure includes: an insertion portion including a distal end portion, a bending portion located proximally relative to the distal end portion; an operation portion detachably attached to a proximal end of the insertion portion; and a bending wire extending from the insertion portion to the operation portion, the bending wire configured to bend the bending portion; and a fitting mechanism configured to connect the insertion portion and the operation portion; and the fitting mechanism including a plate portion, a convex portion located on the plate portion, a first hole configured to fit the convex portion, and a second hole configured to expose at least one of the plate portion and the convex portion to outside, a distal end section of the operation portion and a proximal end section of the insertion portion defines a connection portion, the connection portion includes the fitting mechanism, the fitting mechanism couples the insertion portion and the operation portion by fitting the convex portion and the first hole. When the insertion portion and the operation is connected, the fitting mechanism is located on an outer peripheral surface of the connection portion at a circumferential position corresponding to a circumferential position of the bending wire.

A method of disassembling an endoscope according to another aspect of the present disclosure is a method of disassembling an endoscope including an insertion portion including a bending portion and a bending wire configured to bend the bending portion, an operation portion configured to be detachably attached to the insertion portion, the operation portion located proximally relative to the insertion portion, and a connection portion defined by a distal end section of operation portion and a proximal end section of the insertion portion, configured to connect the insertion portion and the operation portion, and the connection portion includes a fitting mechanism including a plate portion, a convex portion located on the plate portion, a first hole configured to fit the convex portion, and a second hole configured to expose at least one of the plate portion and the convex portion to outside, the fitting mechanism being located on an outer peripheral surface of the connection portion at a circumferential position corresponding to a circumferential position of the bending wire of the insertion portion. The method includes: pushing at least one of the plate portion and the convex portion from the second hole; relatively moving the operation portion and the insertion portion in a state where the convex portion and the first hole are unfitted; and decoupling the insertion portion and the operation portion to separate the insertion portion and the operation portion.

BRIEF DESCRIPTION OF THE DRAWINGS

Figure 1:
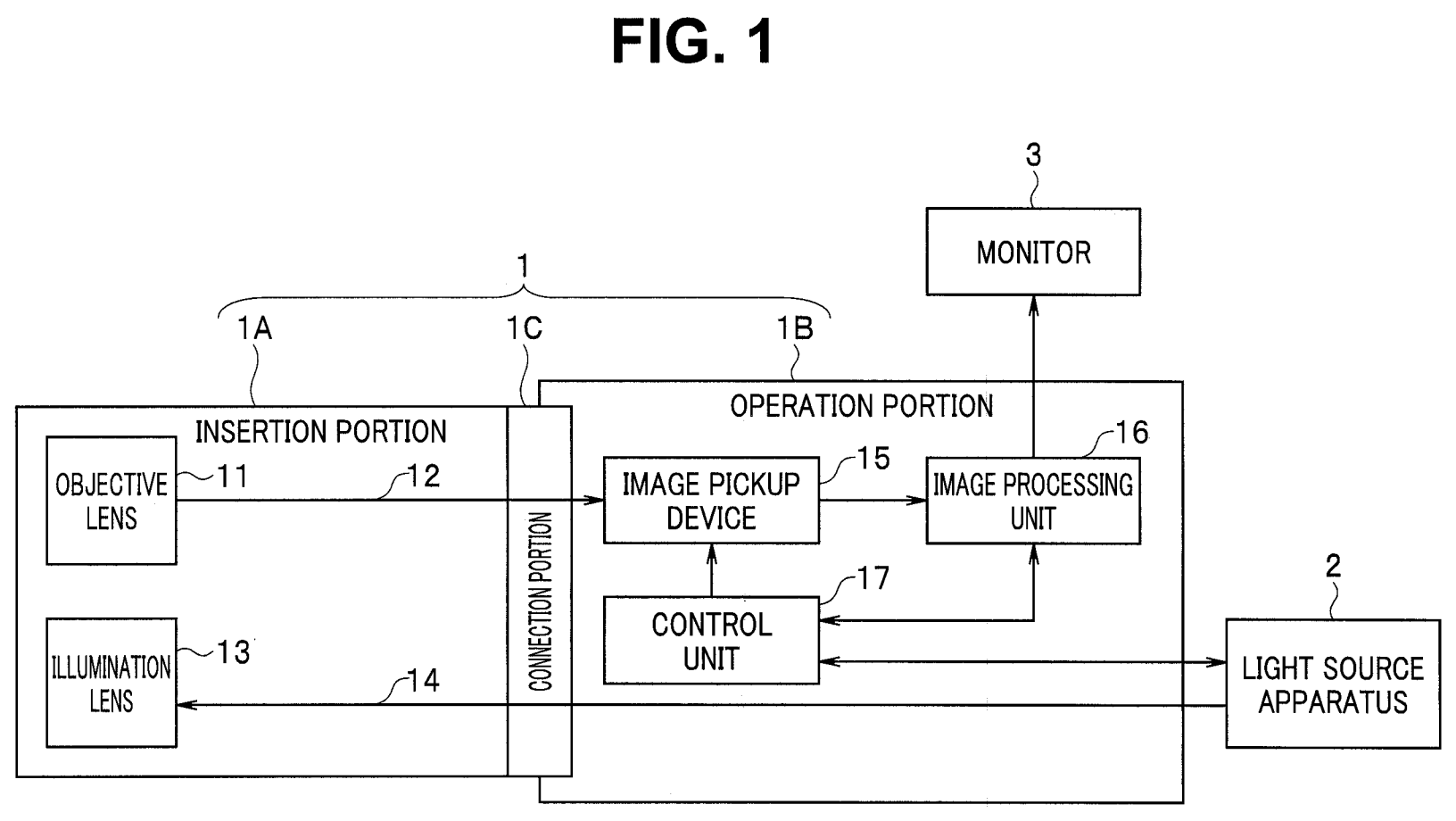

FIG. 1 is a block diagram illustrating a configuration example of an endoscope system according to a first embodiment of the present disclosure.

FIG. 13 is a flowchart illustrating a method of disassembling and collecting the endoscope according to the first embodiment.

DETAILED DESCRIPTION

Figure 2:
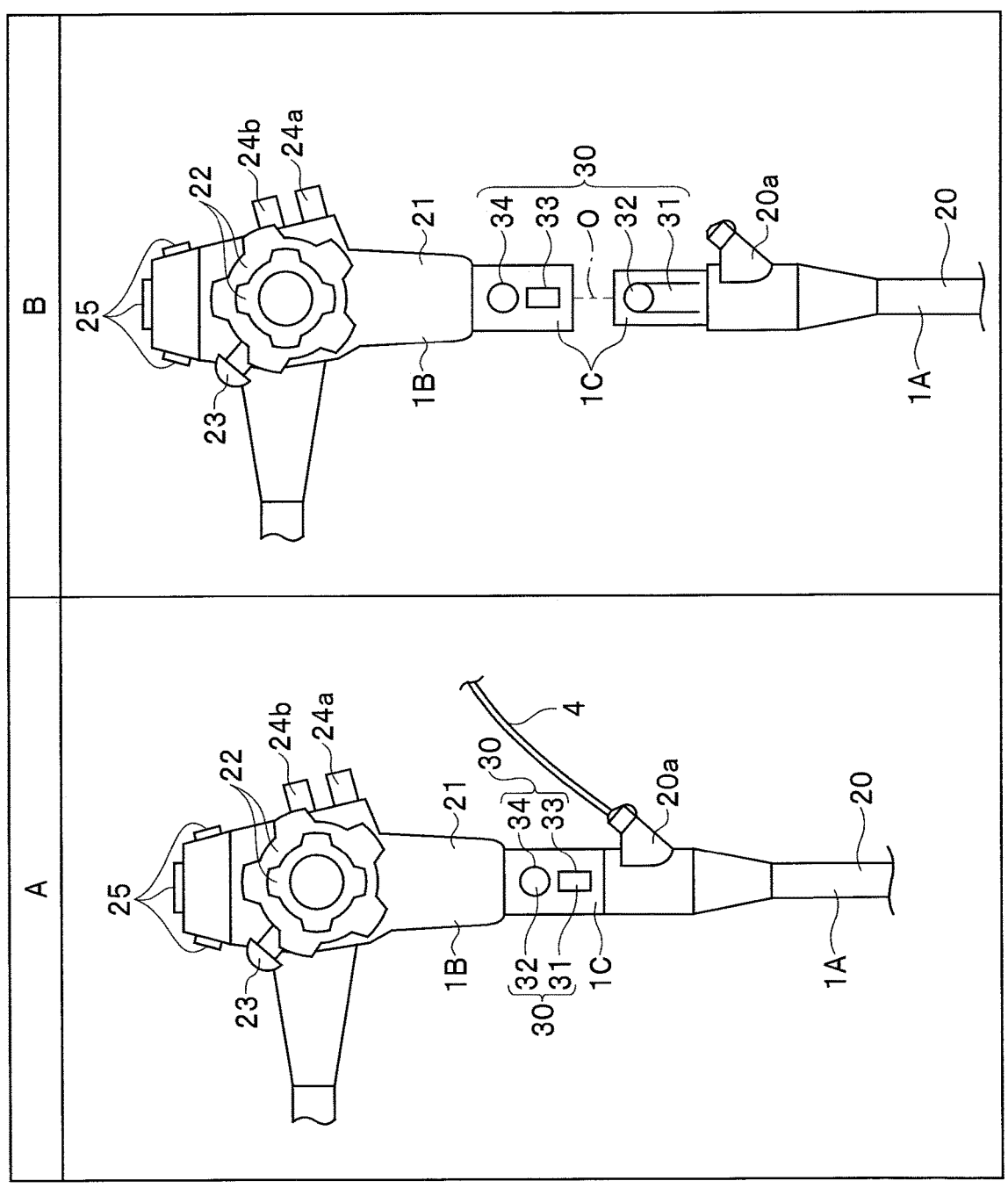
FIG. 2 is a diagram table illustrating a state where an insertion portion and an operation portion are coupled and a state where the insertion portion and the operation portion are decoupled according to the first embodiment.

Although an image pickup device itself as a part is generally usable a plurality of times, the image pickup device is discarded after single use, which increases an environmental load. Therefore, to enable reuse of a part that is usable a plurality of times and is high in cost, a single-use endoscope is preferably configured.

According to embodiments described below, it is possible to provide an endoscope that can reduce the environmental load and is low in cost, and a method of disassembling the endoscope.

The embodiments of the present disclosure are described below with reference to drawings. However, the present disclosure is not limited by the embodiments described below.

Note that, in description of the drawings, the same or corresponding elements are appropriately denoted by the same reference numerals. Further, note that the drawings are schematic, and relationship between lengths of elements, ratios of the lengths of the elements, the number of each of the elements, and the like in one drawing may be different from actual ones for ease of description. Further, a plurality of the drawings may include portions different in relationship and ratios of the lengths from each other.

First Embodiment

FIG. 1 to FIG. 13 illustrate a first embodiment of the present disclosure. FIG. 1 is a block diagram illustrating a configuration example of an endoscope system according to the first embodiment.

The endoscope system includes an endoscope 1, a light source apparatus 2, and a monitor 3. The endoscope 1 is configured as, for example, a hybrid endoscope. The endoscope 1 is connected to the light source apparatus 2 and the monitor 3. The light source apparatus 2 emits illumination light for illuminating a subject. The monitor 3 displays an image acquired by the endoscope 1.

An insertion portion 1A and an operation portion 1B of the endoscope 1 are coupled by a connection portion 1C. The insertion portion 1A and the operation portion 1B coupled by the connection portion 1C can be decoupled. A part of the connection portion 1C is provided in the insertion portion 1A, and the other portion of the connection portion 1C is provided in the operation portion 1B.

The insertion portion 1A includes an objective lens 11, an image guide fiber 12, an illumination lens 13, and a light guide fiber 14.

The objective lens 11 forms an optical image of the subject on a distal end surface of the image guide fiber 12.

The image guide fiber 12 is configured as a fiber bundle obtained by bundling a plurality of optical fibers, for example, thousands to hundreds of thousands of optical fibers. The image guide fiber 12 transmits the optical image formed on the distal end surface by the objective lens 11.

The light guide fiber 14 transmits the illumination light emitted from the light source apparatus 2. The illumination lens 13 irradiates the subject with the illumination light transmitted through the light guide fiber 14.

The operation portion 1B includes an image pickup device 15, an image processing unit 16, and a control unit 17.

The image pickup device 15 is a two-dimensional image pickup device in which a plurality of pixels are two-dimensionally arranged. Examples of the image pickup device 15 include a CCD (charge coupled device) imager and a CMOS (complementary metal oxide semiconductor) imager. The image pickup device 15 photoelectrically converts the optical image transmitted through the image guide fiber 12 to generate an image pickup signal.

The image processing unit 16 receives the image pickup signal generated by the image pickup device 15. The image processing unit 16 performs various kinds of image processing on the image pickup signal to generate an image signal. The image processing unit 16 transmits the image signal to the monitor 3 and an unillustrated image recording apparatus. The monitor 3 receives the image signal and displays an image. The image recording apparatus records the received image signal.

The control unit 17 controls the whole of the endoscope 1 including the image pickup device 15 and the image processing unit 16. Further, the control unit 17 communicates with the light source apparatus 2 and controls the light source apparatus 2.

For example, the control unit 17 receives the image signal processed by the image processing unit 16 or the image pickup signal generated by the image pickup device 15, and calculates brightness of a subject image. Further, the control unit 17 controls an exposure time of the image pickup device 15 and emission intensity of the illumination light of the light source apparatus 2 such that the brightness of the subject image becomes target brightness.

Figure 3:
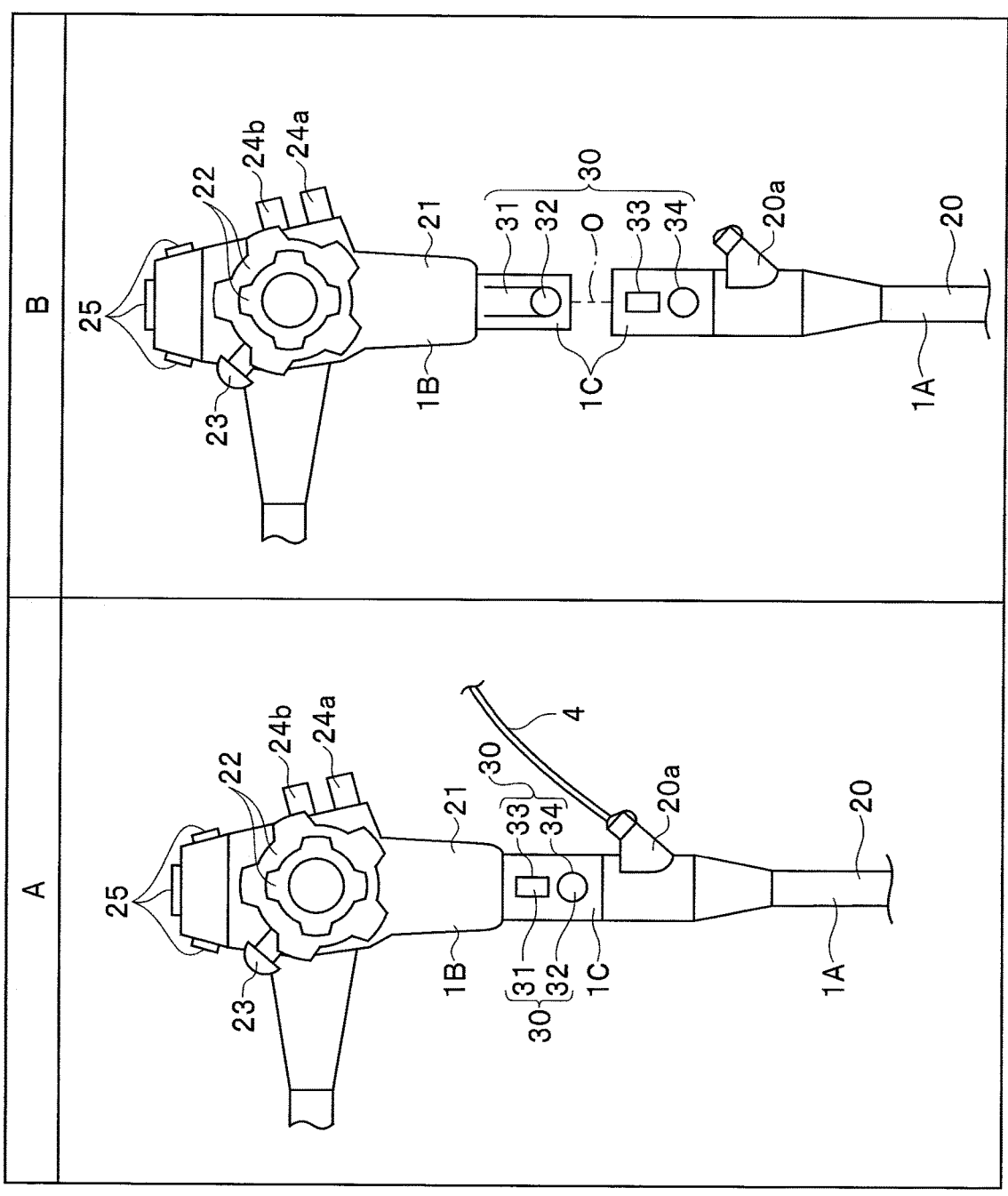
FIG. 3 is a diagram table illustrating the state where the insertion portion and the operation portion are coupled and the state where the insertion portion and the operation portion are decoupled according to a modification of the first embodiment.
Figure 4:
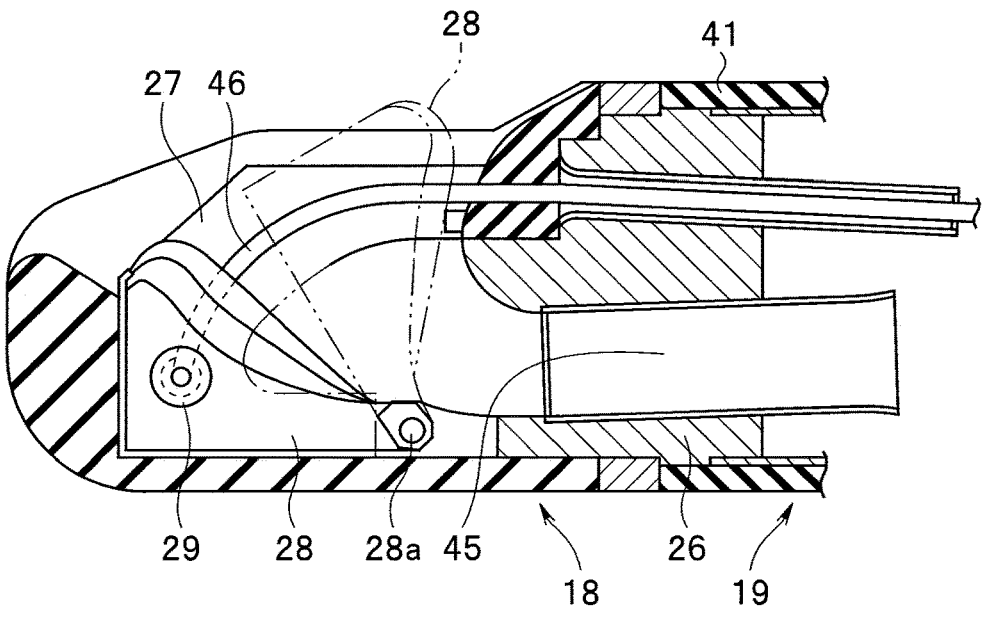
FIG. 4 is a cross-sectional view illustrating a configuration example of a distal end portion of the insertion portion provided with a raising base (forceps elevator) according to the first embodiment.
Figure 5:
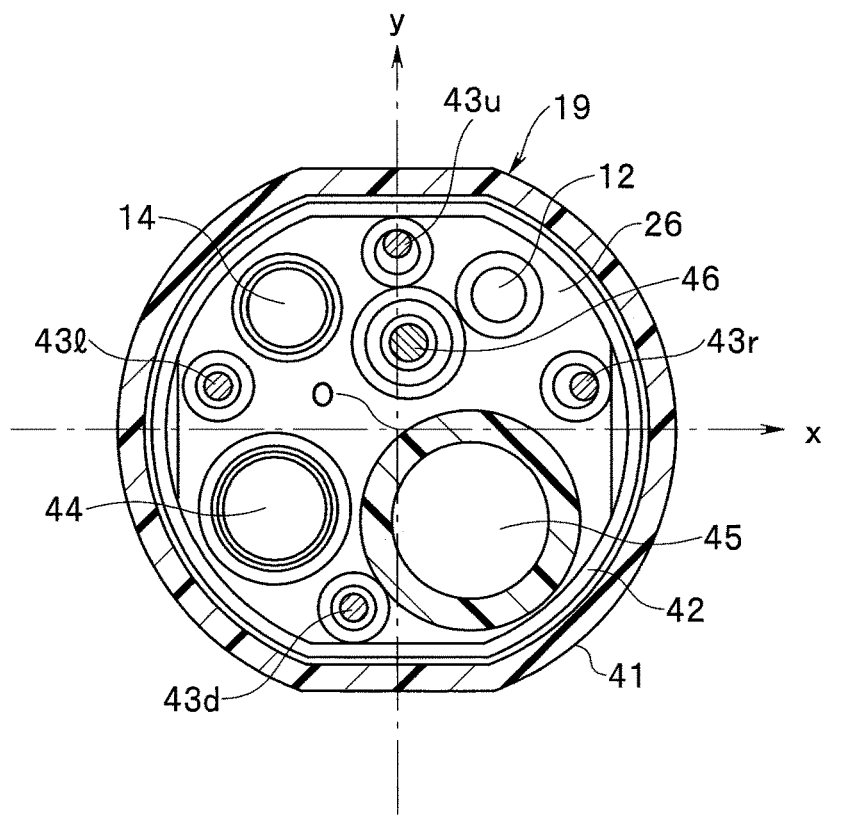
FIG. 5 is a cross-sectional view of a bending portion, perpendicular to a center axis of the insertion portion according to the first embodiment.

The configuration of the endoscope 1 is further described with reference to FIG. 2 to FIG. 5. FIG. 2 is a diagram table illustrating a state where the insertion portion 1A and the operation portion 1B are coupled and a state where the insertion portion 1A and the operation portion 1B are decoupled according to the first embodiment. FIG. 3 is a diagram table illustrating the state where the insertion portion 1A and the operation portion 1B are coupled and the state where the insertion portion 1A and the operation portion 1B are decoupled according to a modification of the first embodiment. FIG. 4 is a cross-sectional view illustrating a configuration example of a distal end portion 18 of the insertion portion 1A provided with a raising base 28 according to the first embodiment. FIG. 5 is a cross-sectional view of a bending portion 19, perpendicular to a center axis O of the insertion portion 1A according to the first embodiment.

As illustrated in FIG. 2 to FIG. 4, the insertion portion 1A includes the distal end portion 18, the bending portion 19, and a flexible tube portion 20 in order from a distal end side toward a proximal end side. The objective lens 11 and the illumination lens 13 are disposed in the distal end portion 18. The bending portion 19 is a bendable portion. The flexible tube portion 20 is a tubular portion having flexibility.

Here, an example in which the endoscope 1 is a soft endoscope including the flexible tube portion 20 is described. However, the endoscope 1 may be a hard endoscope in which a portion corresponding to the flexible tube portion 20 has a hard form.

As illustrated in FIG. 2, FIG. 3, and the like, a treatment instrument insertion port 20a is provided on the proximal end side of the flexible tube portion 20. The treatment instrument insertion port 20a is a proximal end-side opening of a treatment instrument channel 45 (see FIG. 4 and FIG. 5) allowing insertion of a treatment instrument 4.

The operation portion 1B includes a grasping portion 21, two bending operation knobs 22, a treatment instrument raising lever 23, an air/water feeding button 24a, a suction button 24b, and a control button 25.

The grasping portion 21 is a portion for an operator to grasp the endoscope 1 by a hand.

One of the two bending operation knobs 22 is a knob for performing bending operation of the bending portion 19 in an up/down direction, and the other knob 22 is a knob for performing bending operation of the bending portion 19 in a right/left direction. When the bending operation knobs 22 are operated, bending wires 43u, 43d, 43r, and 43l (see FIG. 5) are pulled, and the bending portion 19 is bent.

When the bending portion 19 is bent, a direction of the distal end portion 18 is changed. As a result, an observation direction by the objective lens 11 and an irradiation direction with the illumination light by the illumination lens 13 are changed. The bending portion 19 is also bent in order to improve insertion property of the insertion portion 1A inside the subject.

The treatment instrument raising lever 23 is a lever for raising the raising base 28 (see FIG. 4) inside the distal end portion 18.

The air/water feeding button 24a is a button for operating water feeding to clean the objective lens 11, and air feeding to wipe off the water attached to the objective lens 11. The air/water feeding is performed through the air/water feeding channel 44 (see FIG. 5).

The suction button 24b is a button for performing suction operation inside the subject from the distal end portion 18 through the treatment instrument channel 45.

The control button 25 includes a plurality of buttons such as an operation button relating to image pickup.

As illustrated in FIG. 2 and FIG. 3, the connection portion 1C according to the first embodiment includes, for example, one fitting mechanism 30 (other embodiments in which connection portion 1C includes plurality of fitting mechanisms 30 are described below).

The fitting mechanism 30 includes a plate portion 31 and a convex portion 32. In the present embodiment, the plate portion 31 is provided so as to extend in a direction of the center axis O of the insertion portion 1A. The convex portion 32 is provided at an end part of the plate portion 31 in the direction of the center axis O.

The fitting mechanism 30 further includes a fitted-shape portion to which the convex portion 32 is fitted, and a hole exposing at least one of the plate portion 31 or the convex portion 32 to outside.

The convex portion 32 and the fitted-shape portion of the fitting mechanism 30 are fitted to couple the insertion portion 1A and the operation portion 1B. Further, in the fitting mechanism 30, the insertion portion 1A and the operation portion 1B can be decoupled by pushing at least one of the plate portion 31 or the convex portion 32 from the hole to unfit the convex portion 32 and the fitted-shape portion. Accordingly, the fitting mechanism 30 includes, for example, a snap-fit structure.

The plate portion 31 is formed as, for example, a plate spring by a material having elasticity. The fitting mechanism 30 holds a state where the convex portion 32 and the fitted-shape portion are fitted, by elastic force of the plate portion 31.

One of a set of the plate portion 31 and the convex portion 32 and a set of the fitted-shape portion and the hole is provided on the proximal end side of the insertion portion 1A, and the other set is provided on the distal end side of the operation portion 1B.

FIG. 2 illustrates an example in which the plate portion 31 and the convex portion 32 are provided on the proximal end side of the insertion portion 1A, and the fitted-shape portion and the hole are provided on the distal end side of the operation portion 1B. The convex portion 32 is provided at an end part on the proximal end side of the plate portion 31 in the direction of the center axis O.

FIG. 3 illustrates an example in which the plate portion 31 and the convex portion 32 are provided on the distal end side of the operation portion 1B, and the fitted-shape portion and the hole are provided on the proximal end side of the insertion portion 1A. The convex portion 32 is provided at an end part on the distal end side of the plate portion 31 in the direction of the center axis O.

In the examples illustrated in FIG. 2 and FIG. 3, a hole 33 (second hole) exposing the plate portion 31 to outside is provided, and further, a hole 34 (first hole) also serving as the fitted-shape portion to which the convex portion 32 is fitted and exposing the convex portion 32 to outside is provided. In the example in FIG. 2, the hole 33 is disposed on a side closer to the distal end side than the hole 34 in the direction of the center axis O. In the example in FIG. 3, the hole 33 is disposed on a side closer to the proximal end side than the hole 34 in the direction of the center axis O.

However, it is unnecessary to provide both of the hole 33 and the hole 34, and for example, the hole 33 may be omitted and only the hole 34 may be provided. In this case, in the state where the insertion portion 1A and the operation portion 1B are coupled, the convex portion 32 is exposed to the outside through the hole 34, but the plate portion 31 is not exposed to the outside.

Further, the hole 33 may be provided, and the fitted-shape portion to which the convex portion 32 is fitted may be formed not as a through hole but as a concave portion provided on an inner surface side of an exterior member. In this case, in the state where the insertion portion 1A and the operation portion 1B are coupled, the plate portion 31 is exposed to the outside through the hole 33, but the convex portion 32 is not exposed to the outside.

The plate portion 31 formed as the plate spring gets exhausted (for example, metal fatigue in a case where plate portion 31 is made of metal) due to repetition of elastic deformation in some cases. Therefore, in the configuration in FIG. 2, the plate portion 31 that may get exhausted is provided on the single-use insertion portion 1A, in contrast to the configuration in FIG. 3 in which the plate portion 31 is provided on the operation portion 1B that is to be reused. As a result, the operation portion 1B illustrated in FIG. 2 can be improved in durability in reuse.

As illustrated in FIG. 4, the distal end portion 18 includes a distal end portion main body 26 made of a hard material. The distal end portion main body 26 holds the objective lens 11 and the illumination lens 13. A housing chamber 27 housing the raising base 28 is provided in the distal end portion main body 26.

The housing chamber 27 communicates with the treatment instrument channel 45 provided inside the insertion portion 1A. The housing chamber 27 also serves as a distal end-side opening of the treatment instrument channel 45.

The raising base 28 is pivotably supported to the distal end portion main body 26 by a support shaft 28*a*. A distal end of a raising operation wire 46 is connected to the raising base 28 with a coupling member 29.

A proximal end side of the raising operation wire 46 is inserted into the insertion portion 1A, and is coupled to a mechanism interlocking with the treatment instrument raising lever 23 of the operation portion 1B. When the treatment instrument raising lever 23 is operated, the raising operation wire 46 is pulled, and the raising base 28 is raised.

The treatment instrument 4 having inserted into the treatment instrument channel 45 from the treatment instrument insertion port 20*a* comes into contact with the raising base 28 inside the housing chamber 27, to protrude a distal end portion of the treatment instrument 4 from the housing chamber 27. At this time, when the raising base 28 is raised, the distal end portion of the treatment instrument 4 is also raised together with the raising base 28.

As illustrated in FIG. 5, the bending portion 19 includes a plurality of joint rings 42 pivotably coupled, in an outer skin 41.

The plurality of bending wires 43*u*, 43*d*, 43*r*, and 43*l* bending the bending portion 19 are provided inside the insertion portion 1A. It is assumed that, in a cross-section perpendicular to the center axis O of the insertion portion

1A, a y direction is set in a direction from the center axis O toward the bending wire 43*u*, and an x axis is set in a direction passing through the center axis O and perpendicular to the y axis.

At this time, in the cross-section (xy cross-section) perpendicular to the center axis O of the insertion portion 1A, the bending wire 43*u* bending the bending portion 19 in an up direction is positioned in a positive direction of the y axis, and the bending wire 43*d* bending the bending portion 19 in a down direction is positioned in a negative direction of the y axis. Further, in the xy cross-section, the bending wire 43*r* bending the bending portion 19 in a right direction is positioned in a positive direction of the x axis, and the bending wire 43*l* bending the bending portion 19 in a left direction is positioned in a negative direction of the x axis.

In other words, the bending wire 43*u* and the bending wire 43*d* are provided at opposite positions around the center axis O. The bending wire 43*u* and the bending wire 43*d* configure a first pair bending the bending portion 19 so as to direct the distal end portion 18 in the up/down direction (first direction).

The bending wire 43*r* and the bending wire 43*l* are provided at opposite positions around the center axis O. The bending wire 43*r* and the bending wire 43*l* configure a second pair bending the bending portion 19 so as to direct the distal end portion 18 in the right/left direction (second direction) orthogonal to the up/down direction (first direction). The arrangement around the center axis O of the bending wires 43*u* and 43*d* of the first pair and the arrangement around the center axis O of the bending wires 43*r* and 43*l* of the second pair are different by 90 degrees.

The image guide fiber 12, the light guide fiber 14, the air/water feeding channel 44, the treatment instrument channel 45, and the raising operation wire 46 are also inserted into the insertion portion 1A.

In a layout example illustrated in FIG. 5, the image guide fiber 12 is disposed between the bending wire 43*u* and the bending wire 43*r* (in a case where angle is measured in counterclockwise direction with positive direction of x axis as zero degrees, direction of about 60 degrees). The light guide fiber 14 is disposed between the bending wire 43*u* and the bending wire 43*l* (direction of about 130 degrees). The air/water feeding channel 44 is disposed between the bending wire 43*l* and the bending wire 43*d* (direction of about 220 degrees). The treatment instrument channel 45 is disposed between the bending wire 43*d* and the bending wire 43*r* (direction of about 310 degrees). The raising operation wire 46 is disposed in a direction of the bending wire 43*u* (direction of about 90 degrees).

Figure 6:
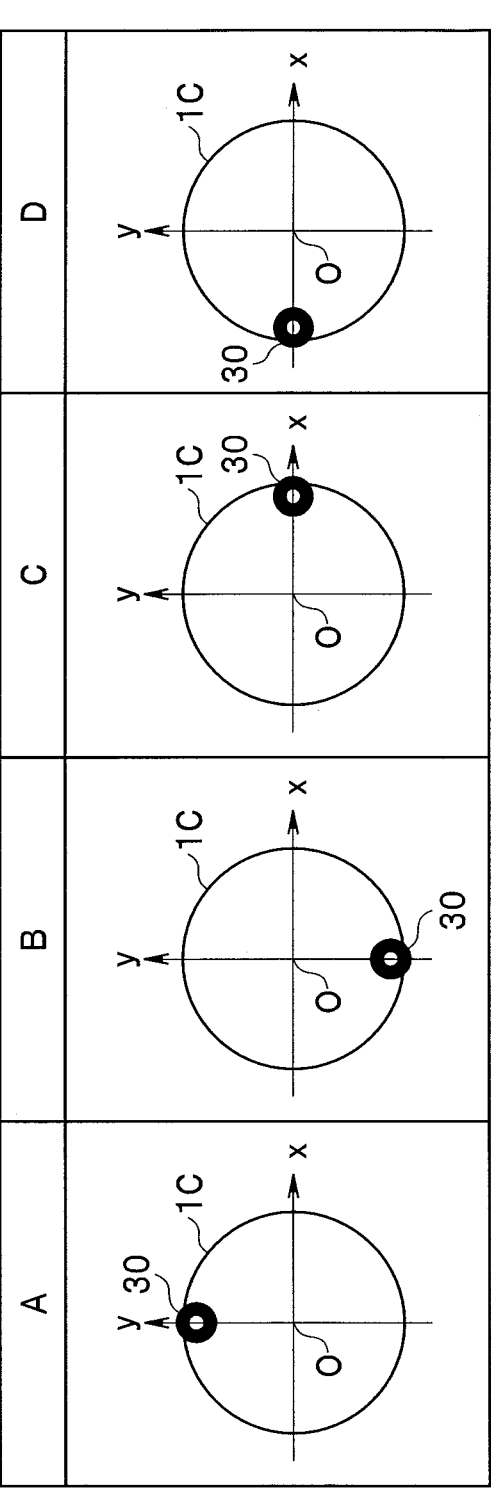
FIG. 6 is a diagram table illustrating arrangement examples of a fitting mechanism in a cross-section perpendicular to the center axis of the insertion portion according to the first embodiment.

FIG. 6 is a diagram table illustrating arrangement examples of the fitting mechanism 30 in the cross-section (xy cross-section) perpendicular to the center axis O of the insertion portion 1A according to the first embodiment. FIG. 6 illustrates the examples in a case where the components inside the insertion portion 1A are arranged as illustrated in FIG. 5.

One fitting mechanism 30 is provided at a position around the center axis O of the insertion portion 1A, corresponding to any of the bending wires 43*u*, 43*d*, 43*r*, and 43*l*.

A field A in FIG. 6 illustrates an example in which the fitting mechanism 30 is provided on a side provided with the bending wire 43*u* (positive direction of y axis). The fitting mechanism 30 is provided at a position around the center axis O, corresponding to the bending wire 43*u* disposed at the position closest to the raising operation wire 46 among the plurality of bending wires 43*u*, 43*d*, 43*r*, and 43*l*, and corresponding to the raising operation wire 46.

A field B in FIG. 6 illustrates an example in which the fitting mechanism 30 is provided on a side provided with the bending wire 43*d* (negative direction of y axis). The fitting mechanism 30 is provided at a position around the center axis O, corresponding to the bending wire 43*d* disposed at the position closest to the treatment instrument channel 45 among the plurality of bending wires 43*u*, 43*d*, 43*r*, and 43*l*, and corresponding to the treatment instrument channel 45.

A field C in FIG. 6 illustrates an example in which the fitting mechanism 30 is provided on a side provided with the bending wire 43*r* (positive direction of x axis), and a field D in FIG. 6 illustrates an example in which the fitting mechanism 30 is provided on a side provided with the bending wire 43*l* (negative direction of x axis).

Figure 7:
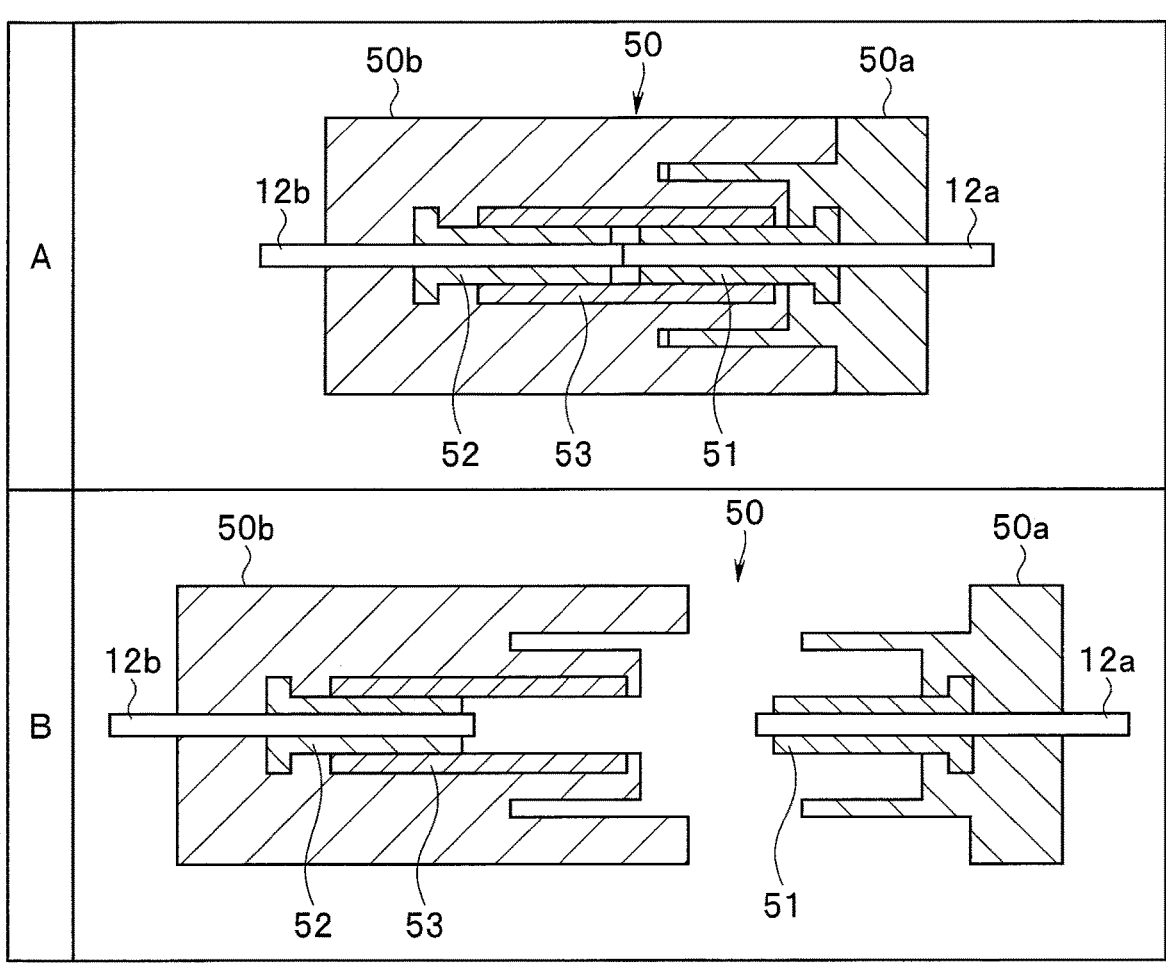
FIG. 7 is a diagram table illustrating configuration examples of an optical connector that relays an optical image transmitted through an image guide fiber, from the insertion portion to the operation portion according to the first embodiment.

FIG. 7 is a diagram table illustrating configuration examples of an optical connector 50 that relays the optical image transmitted through the image guide fiber 12, from the insertion portion 1A to the operation portion 1B according to the first embodiment. Although illustration is omitted, the light guide fiber 14 is also connected by an optical connector having a similar configuration.

The optical connector 50 is provided inside the connection portion 1C.

The optical connector 50 includes a connector 50*a* and a connector receiver 50*b*. The connector 50*a* is provided on one of the proximal end side of the insertion portion 1A and the distal end side of the operation portion 1B, and the connector receiver 50*b* is provided on the other side.

For example, it is assumed that the connector 50*a* is provided on the proximal end side of the insertion portion 1A and the connector receiver 50*b* is provided on the distal end side of the operation portion 1B. In this case, the image guide fiber 12 includes an image guide fiber 12*a* disposed in the insertion portion 1A, and an image guide fiber 12*b* disposed in the operation portion 1B.

The image guide fiber 12*a* is inserted into a ferrule 51 provided in the connector 50*a*.

The image guide fiber 12*b* is inserted into a ferrule 52 provided in a split sleeve 53 of the connector receiver 50*b*.

A field B in FIG. 7 illustrates a state where the connector 50*a* and the connector receiver 50*b* are separated. When the connector 50*a* is inserted into the connector receiver 50*b* from the state, the connector 50*a* and the connector receiver 50*b* are connected as illustrated in a field A in FIG. 7.

By an optical connection structure of the optical connector 50 including the split sleeve 53 and the ferrules 51 and 52, the image guide fiber 12*a* and the image guide fiber 12*b* are positioned so as to transmit the optical image at connection.

A method of disassembling and collecting the endoscope 1 after use is described with reference to FIG. 8 to FIG. 13.

Figure 8:
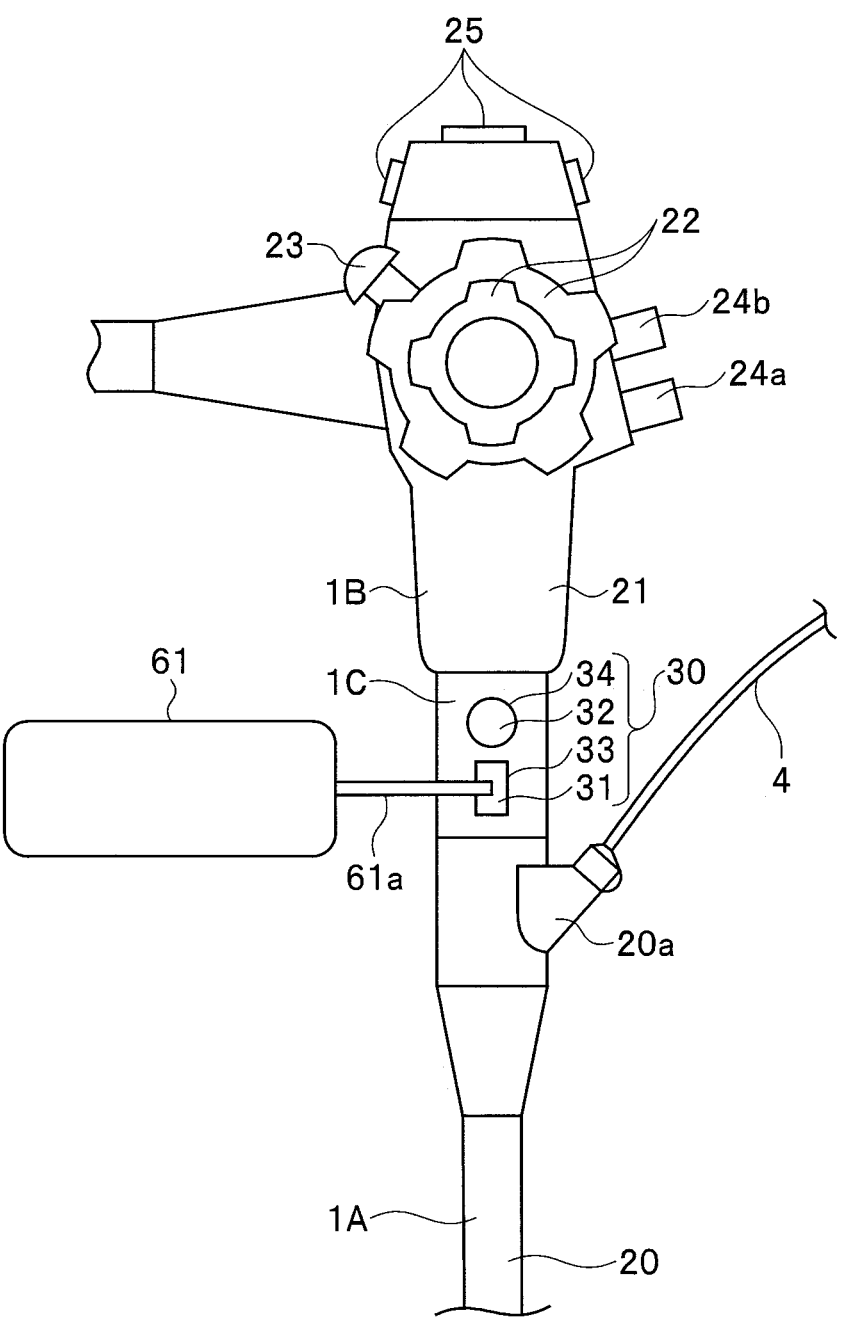
FIG. 8 is a diagram illustrating an example in which the insertion portion and the operation portion coupled by the fitting mechanism is decoupled by a tool according to the first embodiment.
Figure 9:
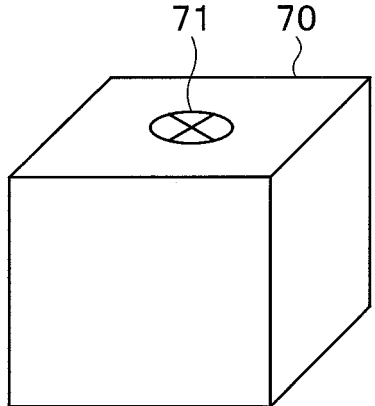
FIG. 9 is a perspective view illustrating a first example of a collection container for collecting the insertion portion after use according to the first embodiment.
Figure 10:
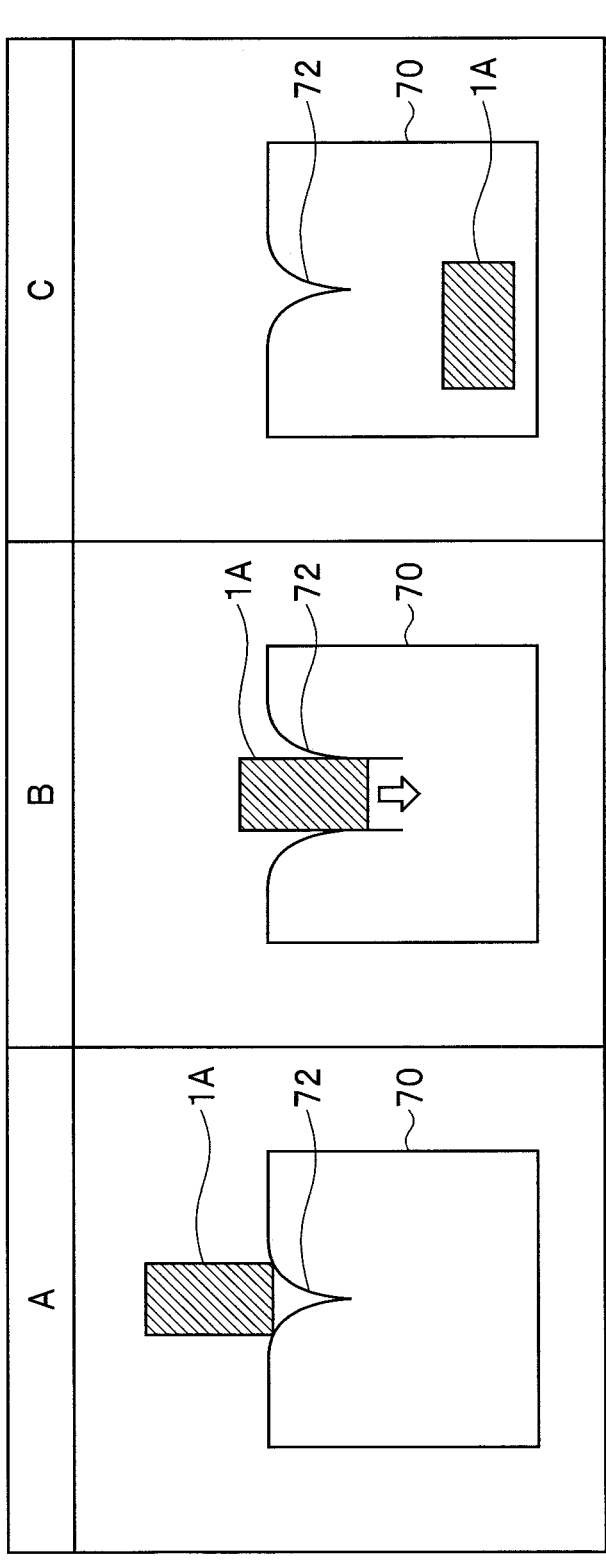
FIG. 10 is a diagram table to explain a second example of the collection container for collecting the insertion portion after use, and a procedure of housing the insertion portion in the collection container according to the first embodiment.
Figure 11:
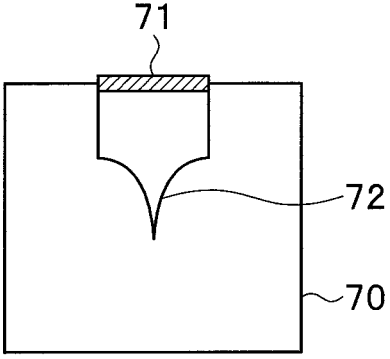
FIG. 11 is a cross-sectional view illustrating a third example of the collection container for collecting the insertion portion after use according to the first embodiment.
Figure 12:
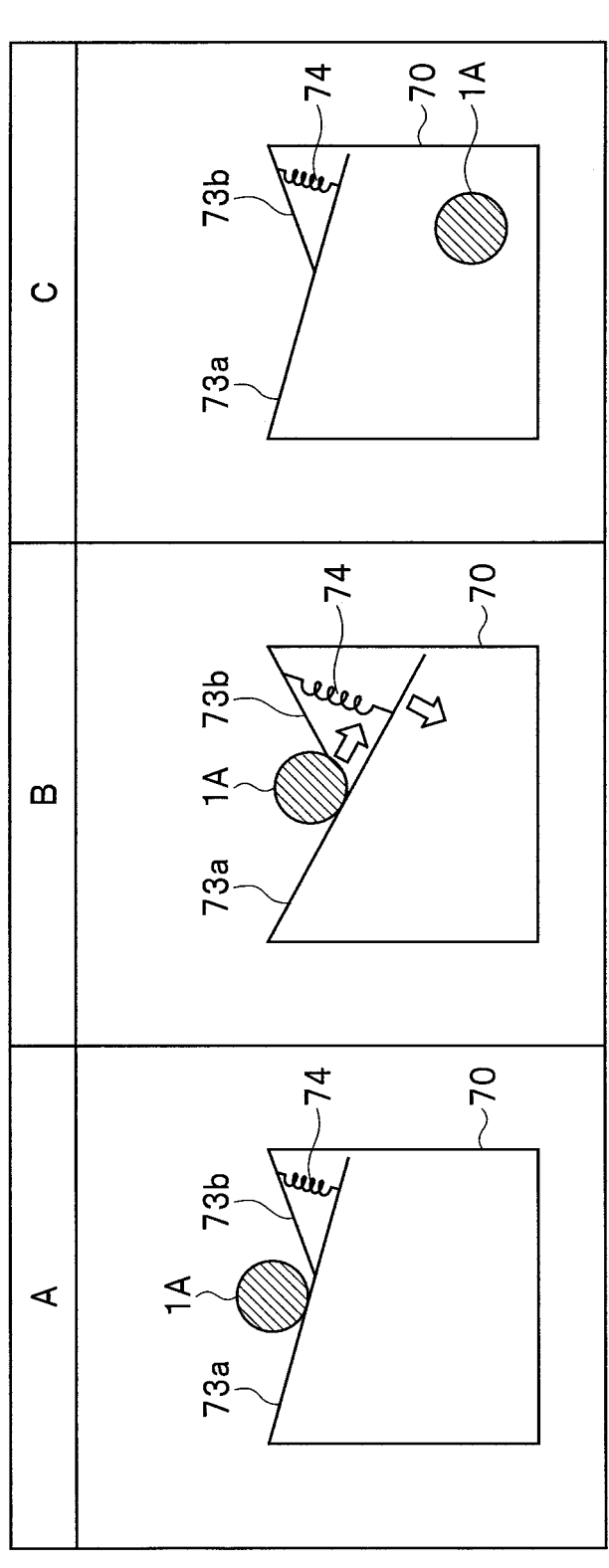
FIG. 12 is a diagram table to explain a fourth example of the collection container for collecting the insertion portion after use, and a procedure of housing the insertion portion in the collection container according to the first embodiment.

FIG. 8 is a diagram illustrating an example in which the insertion portion 1A and the operation portion 1B coupled by the fitting mechanism 30 are decoupled by a tool 61 according to the first embodiment. FIG. 9 is a perspective view illustrating a first example of a collection container 70 for collecting the insertion portion 1A after use according to the first embodiment. FIG. 10 is a diagram table to explain a second example of the collection container 70 for collecting the insertion portion 1A after use, and a procedure of housing the insertion portion 1A in the collection container 70 according to the first embodiment. FIG. 11 is a cross-sectional view illustrating a third example of the collection container 70 for collecting the insertion portion 1A after use according to the first embodiment. FIG. 12 is a diagram table to explain a fourth example of the collection container 70 for collecting the insertion portion 1A after use, and a procedure of housing the insertion portion 1A in the collection container 70 according to the first embodiment. FIG. 13 is a flowchart illustrating the method of disassembling and collecting the endoscope 1 according to the first embodiment.

As illustrated in FIG. 8 and FIG. 13, the endoscope 1 after use is disassembled into the insertion portion 1A and the operation portion 1B.

The tool 61 illustrated in FIG. 8 has a shape similar to, for example, a shape of a screwdriver, and includes a rod-shaped distal end portion 61*a* at a top of a handle.

When processing illustrated in FIG. 13 starts, the convex portion 32 and the hole 34 as the fitted-shape portion are unfitted by pushing the plate portion 31 with the tool 61 from the hole 33 or pushing the convex portion 32 with the tool 61 from the hole 34 (step S1).

In the unfitted state, the operation portion 1B and the insertion portion 1A are pulled in a separating direction and are relatively moved (step S2). As a result, the insertion portion 1A and the operation portion 1B coupled by the fitting mechanism 30 are decoupled, and the operation portion 1B and the insertion portion 1A are separated (step S3).

Before being collected, simple cleaning of the insertion portion 1A is performed (step S4).

The insertion portion 1A that has been simply cleaned is housed in the dedicated collection container 70 from an insertion port (step S5).

After the insertion portion 1A is housed, the insertion port of the collection container 70 is sealed (step S6), the collection container 70 is put on a transportation route and is transported to a manufacturer or a collection trader (step S7), and the processing illustrated in FIG. 13 ends.

The collection container 70 housing the insertion portion 1A is made of a material securing airtightness and strength meeting various kinds of demands for transportation of an infectious waste, for example, stainless steel. The collection container 70 is required to have a structure preventing contents from coming out of the collection container 70 even if the collection container 70 falls down. Therefore, a check valve or the like is provided at the insertion port of the collection container 70. The insertion port of the collection container 70 is sealed in step S6, which realizes the state meeting the various kinds of demands for transportation of the infectious waste.

The inside of the collection container 70 is filled with a substance that can readily sterilize the contents, for example, alcohol. The collection container 70 is installed in each of facilities where inspection by the endoscope 1 is performed.

A configuration example of the collection container 70 is described with reference to FIG. 9 to FIG. 12.

FIG. 9 illustrates the first example of the collection container 70 housing the insertion portion 1A. A film member 71 having, for example, a cross-shaped slit is provided as the insertion port at an upper part of the collection container 70. The film member 71 is made of a material having elasticity such as rubber.

FIG. 10 illustrates the second example of the collection container 70. For example, a flap 72 is provided as the insertion port at the upper part of the collection container 70. The flap 72 is made of a material having elasticity such as rubber. A field A in FIG. 10 illustrates a state where the insertion portion 1A having been simply cleaned is brought close to the flap 72. A field B in FIG. 10 illustrates a state where the insertion portion 1A is pushed into the flap 72. A field C in FIG. 10 illustrates a state where the insertion portion 1A is housed in the collection container 70 and the flap 72 is closed.

FIG. 11 illustrates the third example of the collection container 70. In the collection container 70 of the third example, the film member 71 illustrated in FIG. 9 is provided outside, and the flap 72 illustrated in FIG. 10 is provided inside. Accordingly, the collection container 70 of the third example can maintain high airtightness as compared with the first example and the second example.

FIG. 12 illustrates the fourth example of the collection container 70. A first upper lid 73*a* and a second upper lid 73*b* are provided on an upper surface of the collection container 70 serving as the insertion port. The first upper lid 73*a* and the second upper lid 73*b* are connected by a spring 74. The first upper lid 73*a* is movable to the collection container 70, whereas the second upper lid 73*b* is fixed to the collection container 70. In normal time, the first upper lid 73*a* is pressed against the second upper lid 73*b* by urging force of the spring 74, and the collection container 70 is maintained in a sealed state.

A field A in FIG. 12 illustrates a state where the insertion portion 1A having been simply cleaned is brought close to the first upper lid 73*a*. A field B in FIG. 12 illustrates a state where the insertion portion 1A is pressed against the first upper lid 73*a* to push down the first upper lid 73*a* against the urging force of the spring 74, and a gap is accordingly generated between the first upper lid 73*a* and the second upper lid 73*b*. The insertion portion 1A is pushed into collection container 70 through the gap. A field C in FIG. 12 illustrates a state where the insertion portion 1A is housed in the collection container 70.

According to such a first embodiment, since the connection portion 1C is provided, the insertion portion 1A can be separated from the operation portion 1B, which enables single use of only the insertion portion 1A in place of the whole of the endoscope 1. This makes it possible to reduce an amount of wastes and to contribute to reduction in environmental load.

In particular, when the configuration according to the present embodiment is applied to the endoscope 1 configured as the hybrid endoscope, the operation portion 1B incorporating the expensive image pickup device 15 can be reused, it is unnecessary to discard the image pickup device 15, and a cost when the endoscope 1 is used once can be reduced.

The hybrid endoscope in which an optical image is transmitted from the distal end portion 18 of the insertion portion 1A through the image guide fiber 12. The objective lens 11 is configured to form the optical image on the distal end surface of the image guide fiber 12. The operation portion 1B of the hybrid endoscope includes the image pickup device 15 configured to photoelectrically convert the optical image transmitted through the image guide fiber 12.

Providing the fitting mechanism 30 including the snap-fit structure in the connection portion 1C makes it possible to easily attach/detach the operation portion 1B and the insertion portion 1A.

Further, since the number of provided fitting mechanism 30 is one, the operation portion 1B and the insertion portion 1A can be coupled while the positions of the operation portion 1B and the insertion portion 1A around the center axis O are uniquely determined, which ensures the direction during assembly.

Further, providing the fitting mechanism 30 at the position around the center axis O of the insertion portion 1A, corresponding to the bending wires 43*u*, 43*d*, 43*r*, and 43*l* makes it possible to ensure coupling of the operation portion 1B and the insertion portion 1A.

Second Embodiment

Figure 14:
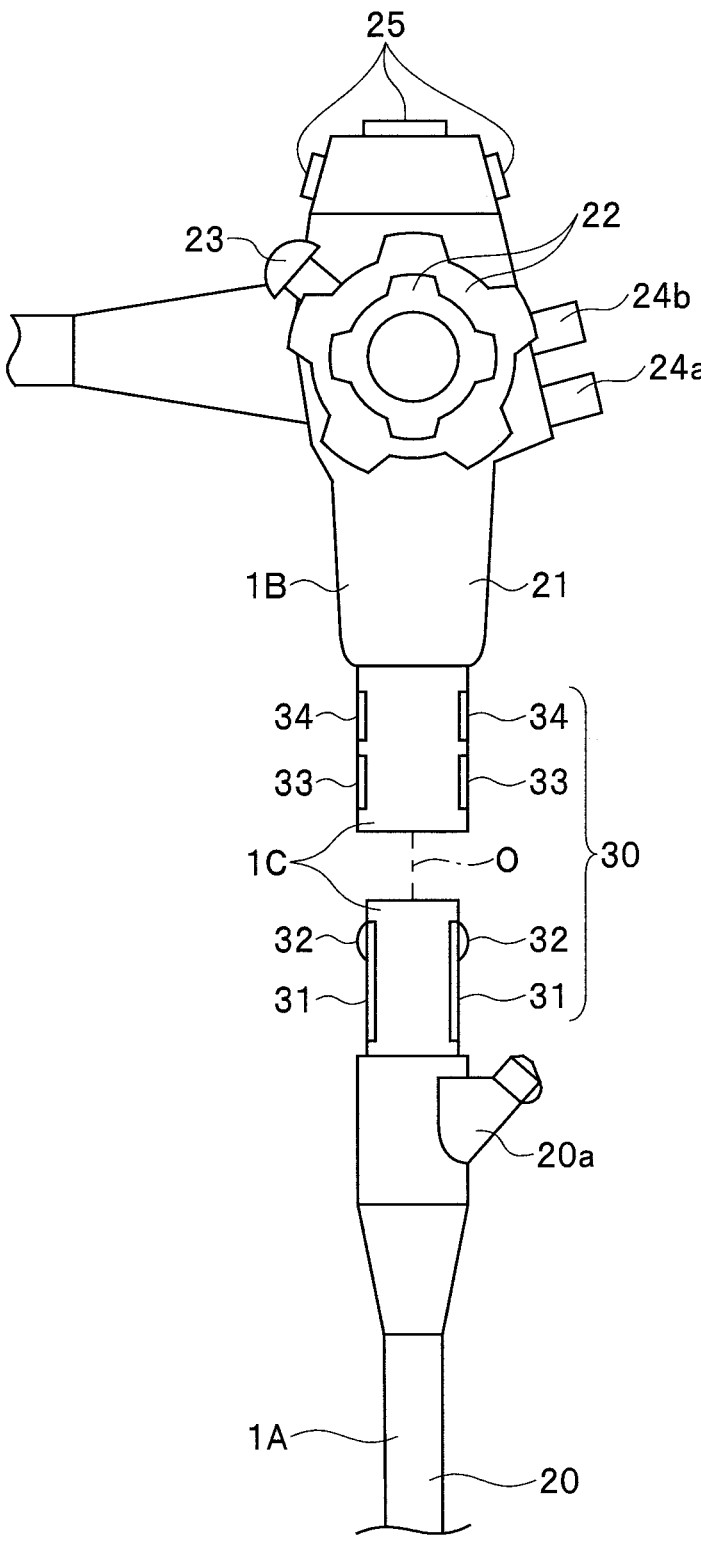
FIG. 14 is a side view illustrating a configuration example of a connection portion according to a second embodiment of the present disclosure.
Figure 15:
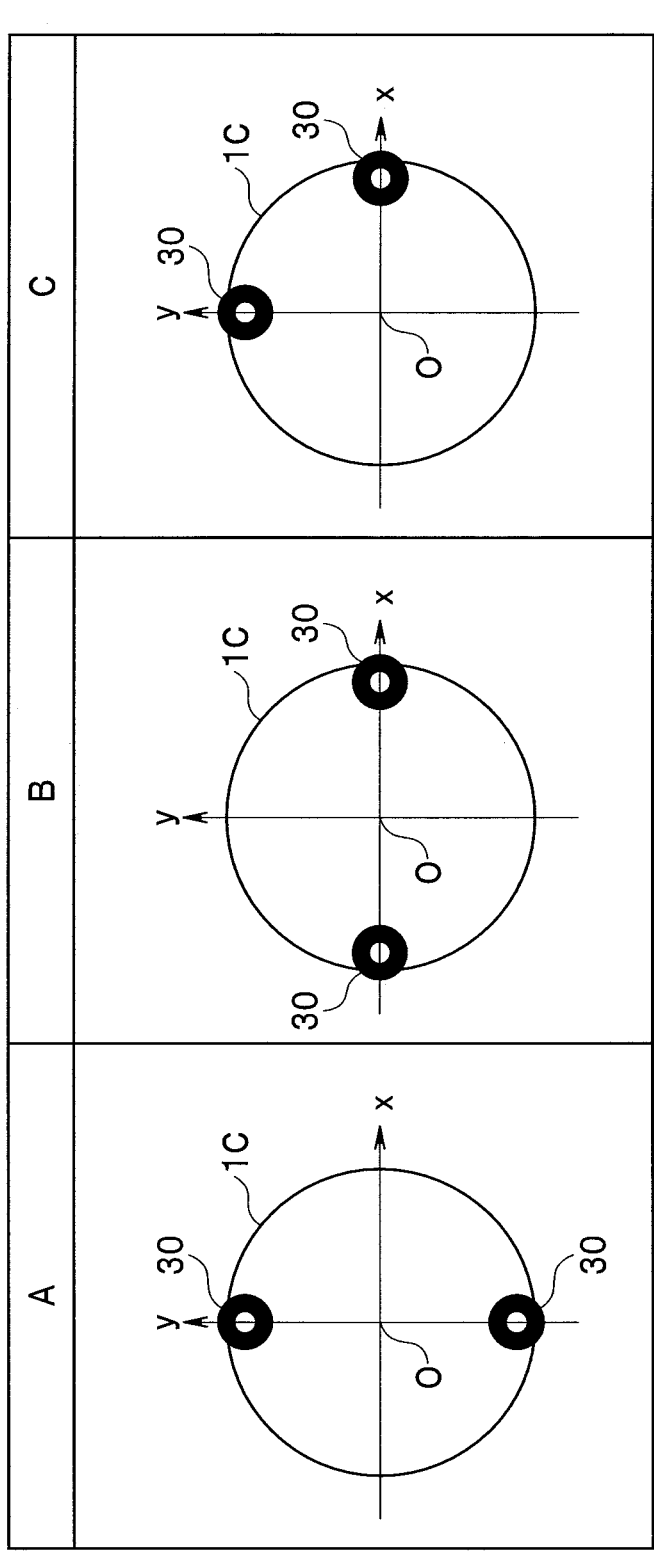
FIG. 15 is a diagram table illustrating arrangement examples of fitting mechanisms in a cross-section perpendicular to a center axis of an insertion portion according to the second embodiment.
Figure 16:
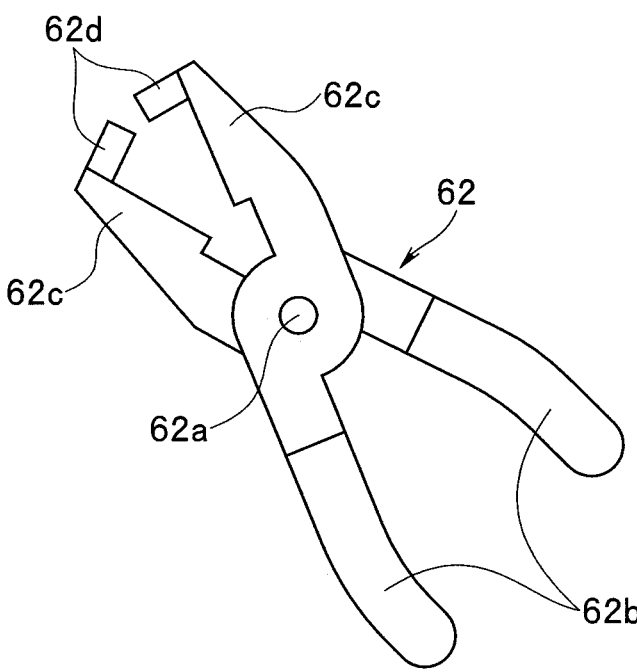
FIG. 16 is a diagram illustrating a configuration example of a dedicated tool for decoupling the insertion portion and an operation portion coupled by the fitting mechanisms according to the second embodiment.

FIG. 14 to FIG. 16 illustrate a second embodiment of the present disclosure. In the second embodiment, portions similar to the portions in the first embodiment are denoted by the same reference numerals, and description of the portions is appropriately omitted. In the second embodiment, differences from the first embodiment are mainly described.

FIG. 14 is a side view illustrating a configuration example of the connection portion 1C according to the second embodiment. In the first embodiment, one fitting mechanism 30 is provided in the connection portion 1C. In the second embodiment, two fitting mechanisms 30 are provided in the connection portion 1C.

As illustrated in FIG. 14, the two fitting mechanisms 30 are provided at different positions around the center axis O. Note that the positions of the two fitting mechanisms 30 in the direction of the center axis O are, for example, identical (may be different).

Each of the fitting mechanisms 30 has the structure same as the structure according to the first embodiment, and includes the plate portion 31, the convex portion 32, the hole 33, and the hole 34.

FIG. 14 illustrates an example in which the holes 33 and the holes 34 are provided on the operation portion 1B, and the plate portions 31 and the convex portions 32 are provided on the insertion portion 1A. However, the plate portions 31 and the convex portions 32 may be provided on the operation portion 1B, and the holes 33 and the holes 34 may be provided on the insertion portion 1A as in the example illustrated in FIG. 3 according to the first embodiment.

In the present embodiment, the components inside the insertion portion 1A are also arranged as illustrated in FIG. 5. Accordingly, the insertion portion 1A includes the four bending wires 43*u*, 43*d*, 43*r*, and 43*l*, and the number of fitting mechanisms 30 is less than or equal to the number of bending wires.

The two fitting mechanisms 30 are provided at positions around the center axis O, corresponding to the plurality of different bending wires 43*u*, 43*d*, 43*r*, and 43*l* among the plurality of bending wires 43*u*, 43*d*, 43*r*, and 43*l*.

FIG. 15 is a diagram table illustrating arrangement examples of the fitting mechanisms 30 in the cross-section (xy cross-section) perpendicular to the center axis O of the insertion portion 1A according to the second embodiment.

A field A in FIG. 15 illustrates an example in which a first fitting mechanism 30 is provided on the side provided with the bending wire 43*u* (positive direction of y axis), and a second fitting mechanism 30 is provided on the side provided with the bending wire 43*d* (negative direction of y axis). In other words, the two fitting mechanisms 30 are provided at opposite positions around the center axis O.

The first fitting mechanism 30 is provided at a position around the center axis O, corresponding to the bending wire 43*u* disposed at the position closest to the raising operation wire 46 among the plurality of bending wires 43*u*, 43*d*, 43*r*, and 43*l*, and corresponding to the raising operation wire 46.

The second fitting mechanism 30 is provided at a position around the center axis O, corresponding to the bending wire 43*d* disposed at the position closest to the treatment instrument channel 45 among the plurality of bending wires 43*u*, 43*d*, 43*r*, and 43*l*, and corresponding to the treatment instrument channel 45.

A field B in FIG. 15 illustrates an example in which the first fitting mechanism 30 is provided on the side provided with the bending wire 43*r* (positive direction of x axis), and the second fitting mechanism 30 is provided on the side provided with the bending wire 43*l* (negative direction of x axis). In this example, the two fitting mechanisms 30 are also provided at opposite positions around the center axis O.

A field C in FIG. 15 illustrates an example in which the first fitting mechanism 30 is provided on the side provided with the bending wire 43*u* (positive direction of y axis), and the second fitting mechanism 30 is provided on the side provided with the bending wire 43*r* (positive direction of x axis). In this example, the two fitting mechanisms 30 are provided at angle positions of 90 degrees with the center axis O in between.

In the example of the field C in FIG. 15, the first fitting mechanism 30 is provided at a position around the center axis O, corresponding to the bending wire 43*u* disposed at the position closest to the raising operation wire 46 among the plurality of bending wires 43*u*, 43*d*, 43*r*, and 43*l*, and corresponding to the raising operation wire 46.

The field C in FIG. 15 illustrates a combination example of (x-axis direction, y-axis direction)=(positive, positive). However, any of combinations (positive, negative), (negative, positive), and (negative, negative) may be adopted.

When the opposite arrangement as illustrated in the field A or B in FIG. 15 is used, the insertion portion 1A and the operation portion 1B are surely coupled as compared with the arrangement illustrated in the field C in FIG. 15. Therefore, the opposite arrangement is preferable.

Note that, in the examples illustrated in the fields A to C in FIG. 15, the two fitting mechanisms 30 are provided at the positions around the center axis O, corresponding to two different bending wires among the four bending wires 43*u*, 43*d*, 43*r*, and 43*l*, but the positions are not limited thereto. In other words, at least one of the two fitting mechanisms 30 may be provided at a position around the center axis O, corresponding to at least one of the plurality of bending wires 43*u*, 43*d*, 43*r*, and 43*l*.

In a case where the arrangement illustrated in the field A or B in FIG. 15 is adopted, an erroneous combination in which the convex portion 32 of the first fitting mechanism 30 is fitted to the hole 34 of the second fitting mechanism 30, and the convex portion 32 of the second fitting mechanism 30 is fitted to the hole 34 of the first fitting mechanism 30 may occur.

To prevent the operation portion 1B and the insertion portion 1A from being coupled at the positions rotated by 180 degrees around the center axis O, the shapes of the convex portion 32 and the hole 34 of the first fitting mechanism 30 are preferably made different from the shapes of the convex portion 32 and the hole 34 of the second fitting mechanism 30.

Some examples of a combination of the different shapes include a combination of an upward triangle and a downward triangle, a combination of an upward semicircle and a downward semicircle, and a combination of a circle and a square. However, the combination of the different shapes is not limited thereto, and the combination of other shapes may be used as a matter of course.

Further, in place of or together with use of the different shapes, the position of the first fitting mechanism 30 in the direction of the center axis O and the position of the second fitting mechanism 30 in the direction of the center axis O may be made different from each other.

FIG. 16 is a diagram illustrating a configuration example of a dedicated tool 62 for decoupling the insertion portion 1A and the operation portion 1B coupled by the fitting mechanism 30 according to the second embodiment.

For example, the tool 62 has a shape similar to a shape of Lineman's pliers. In the tool 62, paired members are pivotable around a shaft 62*a*. Handles 62*b* are provided on one end side of the shaft 62*a*, and jaw portions 62*c* are provided on the other end side. Paired protrusions 62*d* facing each other are provided on respective distal end portions of the paired jaw portions 62*c*.

In the second embodiment, in step S1 in FIG. 13, for example, the paired plate portions 31 are pushed by the paired protrusions 62*d* of the tool 61 from the paired holes 33, to unfit the paired convex portions 32 and the holes 34 as the paired fitted-shape portions. Note that, in step S1, the paired convex portions 32 may be pushed by the paired protrusions 62*d* from the paired holes 34 as described above.

Processing in and after step S2 of the method of disassembling and collecting the endoscope 1 after use is similar to the processing according to the first embodiment.

According to such a second embodiment, it is possible to achieve effects substantially similar to the effects by the above-described first embodiment.

Further, according to the second embodiment, since the insertion portion 1A and the operation portion 1B are fitted by the fitting mechanisms 30 at the two positions around the center axis O, it is possible to enhance fitting strength to some extent, and to reduce backlash to some extent.

Further, according to the second embodiment, the dedicated tool 62 is necessary to disassemble the insertion portion 1A and the operation portion 1B. This makes it possible to prevent the insertion portion 1A and the operation portion 1B from being easily disassembled even when the user tries disassembly.

Third Embodiment

Figure 17:
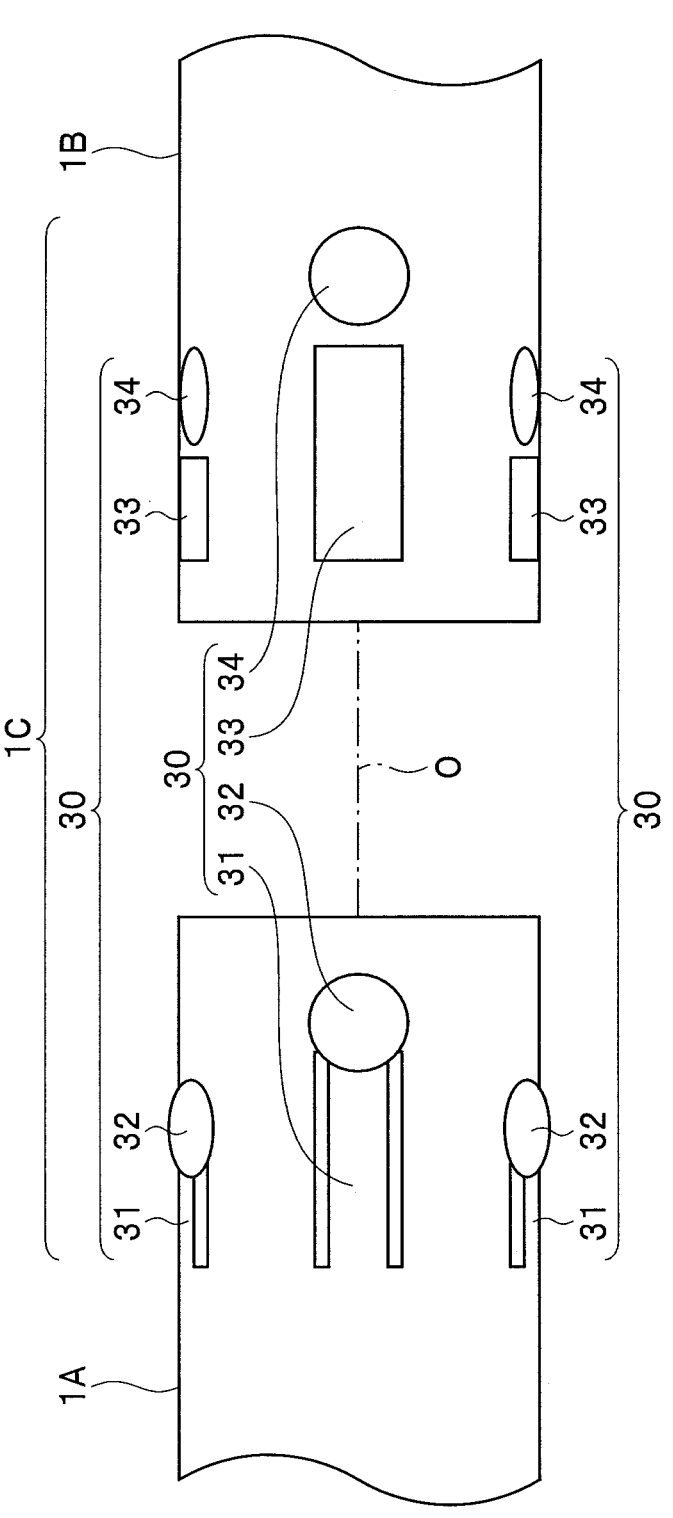
FIG. 17 is a side view illustrating a configuration example of a connection portion according to a third embodiment of the present disclosure.
Figure 18:
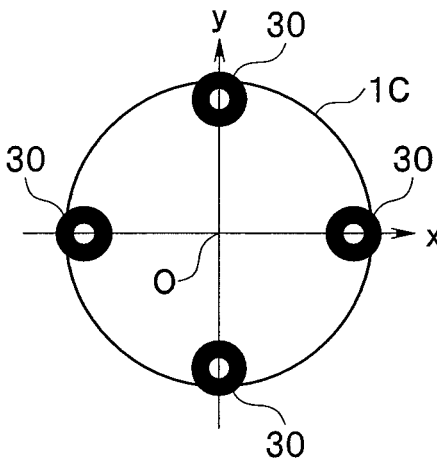
FIG. 18 is a diagram table illustrating an arrangement example of fitting mechanisms in a cross-section perpendicular to a center axis of an insertion portion according to the third embodiment.

FIG. 17 and FIG. 18 illustrate a third embodiment of the present disclosure. In the third embodiment, portions similar to the portions in the first and second embodiments are denoted by the same reference numerals, and description of the portions is appropriately omitted. In the third embodiment, differences from the first and second embodiments are mainly described.

FIG. 17 is a side view illustrating a configuration example of the connection portion 1C according to the third embodiment. One fitting mechanism 30 is provided in the connection portion 1C in the first embodiment, and two fitting mechanisms 30 are provided in the connection portion 1C in the second embodiment. In contrast, in the third embodiment, four fitting mechanisms 30 are provided in the connection portion 1C.

As illustrated in FIG. 17, the four fitting mechanisms 30 are provided at different positions around the center axis O. Each of the fitting mechanisms 30 has a structure basically similar to the structure according to the first embodiment, and includes the plate portion 31, the convex portion 32, the hole 33, and the hole 34.

FIG. 17 illustrates an example in which the holes 33 and the holes 34 are provided on the operation portion 1B, and the plate portions 31 and the convex portions 32 are provided on the insertion portion 1A. However, the plate portions 31 and the convex portions 32 may be provided on the operation portion 1B, and the holes 33 and the holes 34 may be provided on the insertion portion 1A, as in the first and second embodiments.

In the present embodiment, the components inside the insertion portion 1A are also arranged as illustrated in FIG.

5. Accordingly, the insertion portion 1A includes the four bending wires 43u, 43d, 43r, and 43l, and the number of fitting mechanisms 30 is less than or equal to the number of bending wires.

The four fitting mechanisms 30 are provided at respective positions around the center axis O, corresponding to the four bending wires 43u, 43d, 43r, and 43l.

FIG. 18 is a diagram table illustrating an arrangement example of the fitting mechanisms 30 in the cross-section (xy cross-section) perpendicular to the center axis O of the insertion portion 1A according to the third embodiment.

As illustrated in FIG. 18, two fitting mechanisms 30 belonging to a first pair among the four fitting mechanisms 30 are provided at positions around the center axis O, corresponding to the bending wires 43u and 43d of the first pair. In addition, the fitting mechanisms 30 of a second pair configured by the two fitting mechanisms 30 other than the fitting mechanisms 30 of the first pair are provided at positions around the center axis O, corresponding to the bending wires 43r and 43l of the second pair.

Note that, in the example illustrated in FIG. 18, the four fitting mechanisms 30 are provided at the positions around the center axis O, corresponding to the four bending wires 43u, 43d, 43r, and 43l, but the positions are not limited thereto. In other words, at least one of the four fitting mechanisms 30 may be provided at a position around the center axis O, corresponding to at least one of the four bending wires 43u, 43d, 43r, and 43l.

At this time, as illustrated in FIG. 17, the convex portions 32 of the fitting mechanisms 30 of the first pair are provided at first positions in the direction of the center axis O, and the convex portions 32 of the fitting mechanisms 30 of the second pair are provided at second positions different from the first positions in the direction of the center axis O.

Such a difference between the first positions and the second positions is realized by making lengths of the plate portions 31 of the fitting mechanisms 30 of the first pair and lengths of the plate portions 31 of the fitting mechanisms 30 of the second pair different from each other in the direction of the center axis O.

In other words, in any of the first and second pairs, start positions of the plate portions 31 on the distal end side of the insertion portion 1A are the same, but the positions of the convex portions 32 in the direction of the center axis O where the plate portions 31 are terminated are different from each other.

At this time, the lengths of the plate portions 31 of the fitting mechanisms 30 of the first pair may be made longer than the lengths of the plate portions 31 of the fitting mechanisms 30 of the second pair. Further, the lengths of the plate portions 31 of the fitting mechanisms 30 of the second pair may be made longer than the lengths of the plate portions 31 of the fitting mechanisms 30 of the first pair.

Note that differences are not limited to the lengths of the plate portions 31 of the first pair and the lengths of the plate portions 31 of the second pair. The lengths of the plate portions 31 are made equal to each other, and the arrangement in the direction of the center axis O of the fitting mechanisms 30 of the first pair and the arrangement in the direction of the center axis O of the fitting mechanisms 30 of the second pair may be made different from each other.

Further, the four convex portions 32 of the four fitting mechanisms 30 may be provided at the identical positions in the direction of the center axis O, or may be provided at different positions in the direction of the center axis O.

In the present embodiment, to prevent the operation portion 1B and the insertion portion 1A from being coupled at the positions rotated by 180 degrees around the center axis O due to the erroneous combination of the fitting mechanisms 30, the shapes of the convex portion 32 and the hole 34 of the first fitting mechanism 30 belonging to the first pair are preferably made different from the shapes of the convex portion 32 and the hole 34 of the second fitting mechanism 30 belonging to the first pair, as in the second embodiment. Further, the shapes of the convex portion 32 and the hole 34 of a third fitting mechanism 30 belonging to the second pair may be made different from the shapes of the convex portion 32 and the hole 34 of a fourth fitting mechanism 30 belonging to the second pair, as in the second embodiment.

It is unnecessary to make the shapes of the convex portions 32 and the holes 34 of four sets provided in the plurality of, in this example, the four fitting mechanisms 30 different from each other, and it is sufficient to make the shapes of the convex portion 32 and the hole 34 of at least one set different from the shapes of the other sets.

According to such a third embodiment, it is possible to achieve effects substantially similar to the effects by the above-described first and second embodiments.

Further, according to the third embodiment, since the insertion portion 1A and the operation portion 1B are fitted by the fitting mechanisms 30 at the four positions around the center axis O, it is possible to enhance fitting strength, and to reduce backlash.

Even when the user tries to disassemble the endoscope 1, the endoscope 1 cannot be disassembled unless fitting by the four fitting mechanisms 30 is simultaneously unfitted. Further, in a case where the convex portion 32 provided at the different position in the direction of the center axis O is present, the disassembly becomes more difficult. Therefore, in order to disassemble the endoscope 1, it is necessary to use the dedicated tool or to know the disassembling method. This makes it possible to prevent the endoscope 1 from being easily disassembled by the user.

Fourth Embodiment

Figure 19:
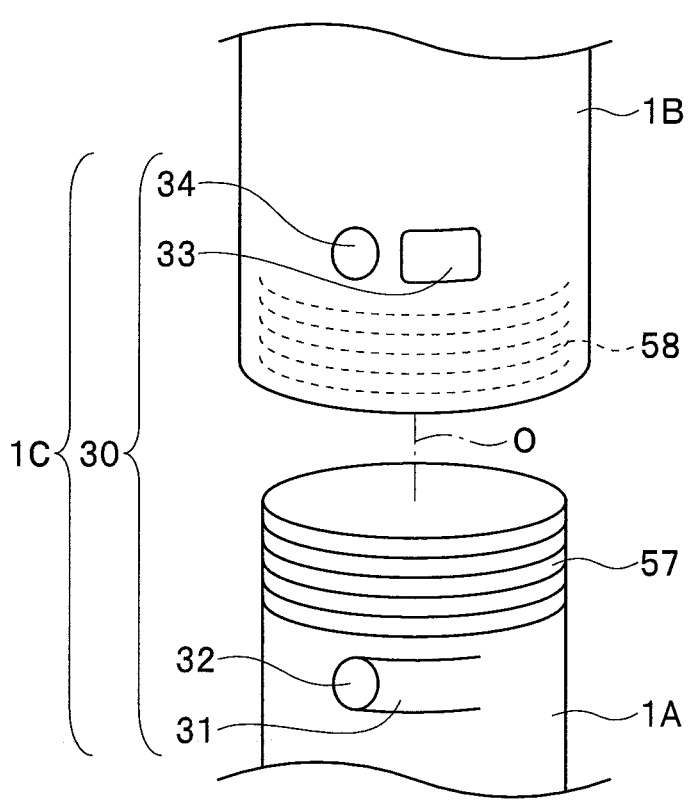
FIG. 19 is a perspective view illustrating a configuration example of a connection portion according to a fourth embodiment of the present disclosure.

FIG. 19 illustrates a fourth embodiment of the present disclosure. In the fourth embodiment, portions similar to the portions in the first to third embodiments are denoted by the same reference numerals, and description of the portions is appropriately omitted. In the fourth embodiment, differences from the first to third embodiments are mainly described.

FIG. 19 is a perspective view illustrating a configuration example of the connection portion 1C according to the fourth embodiment.

The fitting mechanism 30 provided in the connection portion 1C further includes a male screw 57 and a female screw 58 around the center axis O.

The male screw 57 is provided on one of the proximal end side of the insertion portion 1A and the distal end side of the operation portion 1B, and the female screw 58 is provided on the other side. In the example illustrated in FIG. 19, the male screw 57 is provided on the proximal end side of the insertion portion 1A, and the female screw 58 is provided on the distal end side of the operation portion 1B. Alternatively, the female screw 58 may be provided on the proximal end side of the insertion portion 1A, and the male screw 57 may be provided on the distal end side of the operation portion 1B.

In the present embodiment, the plate portion 31 is provided so as to extend circumferentially or helically around the center axis O. The convex portion 32 is provided at an end part of the plate portion 31 around the center axis O.

In such a configuration, the insertion portion 1A and the operation portion 1B are relatively rotated around the center axis O to fasten the male screw 57 and the female screw 58. As a result, the convex portion 32 and the hole 34 (fitted-shape portion) are fitted, and the insertion portion 1A and the operation portion 1B are coupled.

To disassemble the insertion portion 1A and the operation portion 1B, the male screw 57 and the female screw 58 are rotated in a direction opposite to a fastening direction in a state where the convex portion 32 and the hole 34 (fitted-shape portion) are unfitted.

According to such a fourth embodiment, it is possible to achieve effects substantially similar to the effects by the above-described first to third embodiments.

Further, according to the fourth embodiment, since the insertion portion 1A and the operation portion 1B are coupled by fastening the male screw 57 and the female screw 58, it is possible to reduce backlash.

Figure 20:
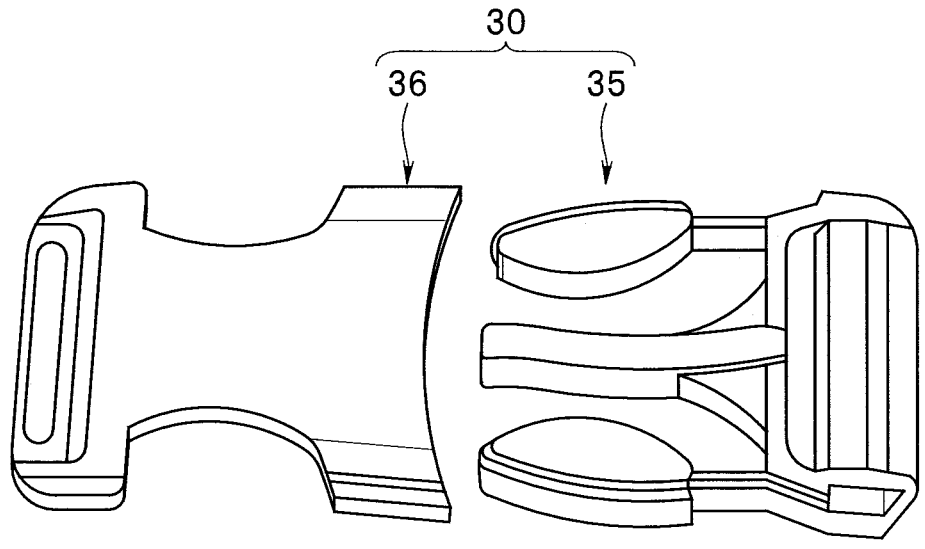
FIG. 20 is a diagram illustrating a modification of the fitting mechanism according to each of the above-described embodiments.

FIG. 20 is a diagram illustrating a modification of the fitting mechanism 30 according to each of the above-described embodiments.

The example in which the fitting mechanism 30 includes the snap-fit structure is described above. However, the present disclosure is not limited thereto.

For example, as illustrated in FIG. 20, the fitting mechanism 30 including a side-release buckle structure may be used. In this case, the fitting mechanism 30 includes a male structure portion 35 and a female structure portion 36. When the male structure portion 35 is inserted into the female structure portion 36, the female structure portion 36 and the male structure portion 35 are coupled. When sides are pressed, the female structure portion 36 and the male structure portion 35 are decoupled.

One of the male structure portion 35 and the female structure portion 36 is disposed in the insertion portion 1A, and the other is disposed in the operation portion 1B.

Further, the structure of the fitting mechanism 30 is not limited to the side-release buckle structure, and the fitting mechanism 30 including a front-release buckle structure in which a front portion is pressed to decouple the female structure portion and the male structure portion may be used.

The present disclosure is not limited to the above-described embodiments. The present disclosure can be embodied while the components are deformed without departing from the gist of the disclosure. Further, the plurality of components disclosed in the above-described embodiments can be appropriately combined to form various aspects of the disclosure. For example, some of the components disclosed in each of the embodiments may be removed. Further, the components of the different embodiments may be appropriately combined. As described above, various modifications and applications can be made without departing from the spirit of the disclosure as a matter of course.

What is claimed is:

1. An endoscope, comprising:
an insertion portion including a distal end portion, a bending portion located proximally relative to the distal end portion;
an operation portion detachably attached to a proximal end of the insertion portion;
a bending wire extending from the insertion portion to the operation portion, the bending wire configured to bend the bending portion; and
a fitting mechanism configured to connect the insertion portion and the operation portion,
wherein the fitting mechanism includes:
a plate portion;

a convex portion located on the plate portion;
a first hole configured to fit the convex portion; and
a second hole configured to expose at least one of the plate portion and the convex portion to outside of the fitting mechanism,
wherein a distal end section of the operation portion and a proximal end section of the insertion portion defines a connection portion,
wherein the connection portion includes the fitting mechanism,
wherein the fitting mechanism couples the insertion portion and the operation portion by fitting the convex portion and the first hole, and
wherein, when the insertion portion and the operation portion are connected, the fitting mechanism is located on an outer peripheral surface of the connection portion at a circumferential position corresponding to a circumferential position of the bending wire.

2. The endoscope according to claim 1, wherein the distal end section of the operation portion is a first part of the connection portion and the proximal end section of the insertion portion is a second part of the connection portion, and
wherein the plate portion and the convex portion are located on the first part of the connection portion and the first hole and the second hole are located on the second part of the connection portion, or the first hole and the second hole are located on the first part of the connection portion and the plate portion and the convex portion are located on the second part of the connection portion.

3. The endoscope according to claim 1, wherein the plate portion provides a bias force to fit the convex portion into the first hole.

4. The endoscope according to claim 1, wherein the insertion portion includes a plurality of bending wires and a plurality of fitting mechanisms, and
wherein at least one of the plurality of fitting mechanisms is located at a circumferential position around a center axis of the plurality of fitting mechanisms corresponding to a circumferential position of at least one of the plurality of bending wires.

5. The endoscope according to claim 4, wherein a number of the plurality of fitting mechanisms is less than or equal to a number of the plurality of bending wires, and
wherein circumferential positions around the center axis of the plurality of fitting mechanisms correspond to circumferential positions of the plurality of bending wires.

6. The endoscope according to claim 5, wherein the plurality of bending wires includes two bending wires provided at opposite positions around the center axis,
wherein the number of the plurality of fitting mechanisms is two, and
wherein the two fitting mechanisms are located at circumferential positions around the center axis corresponding to circumferential positions of the two bending wires.

7. The endoscope according to claim 5, wherein the plurality of bending wires includes two bending wires of a first pair and two bending wires of a second pair,
wherein the first pair bend the bending portion to direct the distal end portion in a first direction, and the second pair bend the bending portion to direct the distal end portion in a second direction, the second direction orthogonal to the first direction, wherein the number of the plurality of fitting mechanisms is four, wherein, among the four fitting mechanisms, two fitting mechanisms of a first set are located at circumferential positions around the center axis corresponding to circumferential positions of the bending wires of the first pair, and wherein, among the four fitting mechanisms, two fitting mechanisms of a second set are located at circumferential positions around the center axis corresponding to circumferential positions of the bending wires of the second pair.

8. The endoscope according to claim 7, wherein the convex portions of the four fitting mechanisms are located at identical positions in a direction of the center axis.

9. The endoscope according to claim 7, wherein the convex portions of the fitting mechanisms of the first set are located at first positions in a direction of the center axis, wherein the convex portions of the fitting mechanisms of the second set are located at second positions in the direction of the center axis, and wherein the first positions are different from the second positions.

10. The endoscope according to claim 9, wherein the plate portions extend in the direction of the center axis, wherein the convex portions are located at respective ends of the plate portions in the direction of the center axis, wherein the plate portions of the fitting mechanisms of the first set have a first length in the direction of the center axis and the plate portions of the fitting mechanisms of the second set have a second length in the direction of the center axis, and wherein the first length is different from the second length.

11. The endoscope according to claim 4, wherein at least one of the convex portions located in the plurality of fitting mechanisms has a shape different from shapes of other convex portions.

12. The endoscope according to claim 1, wherein the insertion portion includes:

a treatment instrument channel allowing insertion of a treatment instrument, and wherein the fitting mechanism is located at a circumferential position around the center axis corresponding to a circumferential position of the bending wire disposed at a position closest to the treatment instrument channel among the plurality of bending wires and corresponding to the treatment instrument channel.

13. The endoscope according to claim 1, wherein the fitting mechanism further includes a male thread located on one of the first part or the second part of the connection portion, and a female thread located on the other of the first part or the second part of the connection portion, wherein the plate portion is located to extend circumferentially of helically around the center axis, wherein the convex portion is located at an end part of the plate portion around the center axis, and wherein the convex portion and the first hole are fitted and the insertion portion and the operation portion are coupled by relatively rotating the insertion portion and the operation portion around the center axis to fasten the male thread and the female thread.

14. The endoscope according to claim 1, wherein the insertion portion and the operation portion coupled by the fitting mechanism are decoupled, and the operation portion and the insertion portion are separated, by pushing at least one of the plate portion and the convex portion to unfit the convex portion from the first hole, and then relatively moving the operation portion and the insertion portion.

15. The endoscope according to claim 1, wherein the endoscope is a hybrid endoscope, wherein the insertion portion further includes an image guide fiber configured to transmit an optical image, and an objective lens configured to form the optical image on a distal end surface of the image guide fiber, wherein the operation portion includes an image pickup device configured to photoelectrically convert the optical image transmitted through the image guide fiber, wherein the endoscope further includes an optical connector configured to relay the optical image from the insertion portion to the operation portion, and wherein the optical connector includes a connector provided on one side of the proximal end side of the insertion portion and the distal end side of the operation portion, and a connector receiver provided on another side.

16. A method of disassembling the endoscope of claim 1, the method comprising:

pushing at least one of the plate portion and the convex portion from the second hole;

relatively moving the operation portion and the insertion portion in a state where the convex portion and the first hole are unfitted; and decoupling the first part of the connection portion and the second part of the connection portion to separate the insertion portion and the operation portion.

17. The endoscope according to claim 1, wherein the insertion portion and the operation portion are decoupled by pushing at least one of the plate portion and the convex portion to unfit the convex portion and the first hole.

18. An endoscope, comprising:

an insertion portion including a distal end portion, a bending portion located proximally relative to the distal end portion;

an operation portion detachably attached to a proximal end of the insertion portion;

a plurality of bending wires extending from the insertion portion to the operation portion, the plurality of bending wires configured to bend the bending portion; and a fitting mechanism configured to connect the insertion portion and the operation portion, wherein the fitting mechanism includes:

a plate portion;

a convex portion located on the plate portion;

a first hole configured to fit the convex portion; and a second hole configured to expose at least one of the plate portion and the convex portion to outside of the fitting mechanism, wherein the insertion portion includes:

a treatment instrument channel allowing insertion of a treatment instrument; and a raising operation wire configured to pull a raising base raising a distal end portion of the treatment instrument, wherein a distal end section of the operation portion and a proximal end section of the insertion portion defines a connection portion, wherein the connection portion includes the fitting mechanism, wherein the fitting mechanism couples the insertion portion and the operation portion by fitting the convex portion and the first hole, and wherein, when the insertion portion and the operation portion are connected, the fitting mechanism is located on an outer peripheral surface of the connection portion at a first circumferential position around the center axis corresponding to a circumferential position of one bending wire of the plurality of bending wires that is disposed at a position closest to the raising operation wire among the plurality of bending wires and corresponding to the raising operation wire.

19. A method of disassembling an endoscope, the endoscope including:

an insertion portion including a bending portion and a bending wire configured to bend the bending portion, an operation portion detachably attached to a proximal end of the insertion portion, and a fitting mechanism configured to connect the insertion portion and the operation portion, the fitting mechanism including a plate portion, a convex portion located on the plate portion, a first hole configured to fit the convex portion, and a second hole configured to expose at least one of the plate portion and the convex portion to outside of the fitting mechanism, a distal end section of the operation portion and a proximal end section of the insertion portion defining a connection portion, the connection portion including the fitting mechanism, the fitting mechanism located on an outer peripheral surface of the connection portion at a circumferential position corresponding to a circumferential position of the bending wire around a center axis of the insertion portion, the method comprising:

pushing at least one of the plate portion and the convex portion from the second hole;

relatively moving the operation portion and the insertion portion in a state where the convex portion and the first hole are unfitted; and decoupling the insertion portion and the operation portion to separate the insertion portion and the operation portion.

20. The method of disassembling the endoscope according to claim 19, wherein relative movement of the operation portion and the insertion portion to decouple the insertion portion and the operation portion is performed by pulling the insertion portion and the operation portion in a separating direction.

* * * * *